(12) United States Patent
Lee et al.

(10) Patent No.: US 10,100,332 B2
(45) Date of Patent: Oct. 16, 2018

(54) BIOLOGICALLY ACTIVE SYNTHETIC NANOPARTICLE CONSTRUCTS AND METHODS OF USE THEREOF

(71) Applicant: Rutgers, The State University of New Jersey, New Brunswick, NJ (US)

(72) Inventors: Ki-Bum Lee, Monmouth Junction, NJ (US); Sahishnu Patel, Lake Hiawatha, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/913,804

(22) PCT Filed: Aug. 25, 2014

(86) PCT No.: PCT/US2014/052569
§ 371 (c)(1),
(2) Date: Feb. 23, 2016

(87) PCT Pub. No.: WO2015/027243
PCT Pub. Date: Feb. 26, 2015

(65) Prior Publication Data
US 2017/0107538 A1    Apr. 20, 2017

Related U.S. Application Data

(60) Provisional application No. 61/947,898, filed on Mar. 4, 2014, provisional application No. 61/869,284, filed on Aug. 23, 2013.

(51) Int. Cl.
*C12N 15/87*    (2006.01)

(52) U.S. Cl.
CPC .......... *C12N 15/87* (2013.01); *C12N 2810/40* (2013.01)

(58) Field of Classification Search
None
See application file for complete search history.

(56) References Cited

U.S. PATENT DOCUMENTS

| | | |
|---|---|---|
| 2005/0176647 A1 | 8/2005 | Sugiyama et al. |
| 2009/0047272 A1 | 2/2009 | Appelbaum et al. |
| 2010/0316702 A1 | 12/2010 | Briggs et al. |

FOREIGN PATENT DOCUMENTS

WO    2013/059831 A1    4/2013

OTHER PUBLICATIONS

Timmers, et al. (1999) "Nuclear and nucleolar localization of *Sacchromyces cerevisiae* ribosomal proteins S22 and S25", FEBS Letters, 452: 335-340.*
Ragin, et al. (2002) "Cellular Import Mediated by Nuclear Localization Signal Peptide Sequences" Chemistry & Biology, 8: 943-48.*
Agbasi-Porter, Chiamaka et al., Transcription Inhibition Using Oligonucleotide-Modified Gold Nanoparticles, Bioconjugate Chemistry, vol. 17, No. 5, Sep. 1, 2006, pp. 1178-1183.
Extended European Search Report dated Jan. 31, 2017 in European Patent Application No. 14837321.0 (8 pages).
Liu, Yang et al., Delivery of Intact Transcription Factor by Using Self-Assembled Supramolecular Nanoparticles, Angewandte Chemie International Edition, vol. 50, No. 13, Mar. 21, 2011, pp. 3058-3062.
Patel, Sahishnu et al., NanoScript: A Nanoparticle-Based Artificial Transcription Factor for Effective Gene Regulation, ACS Nano, vol. 8, No. 9, Aug. 18, 2014, pp. 8959-8967.
Xiao, Xiangshu et al., A Cell-Permeable Synthetic Transcription Factor Mimic, Angewandte Chemie International Edition, vol. 46, No. 16, Apr. 13, 2007, pp. 2865-2868.

* cited by examiner

*Primary Examiner* — Robert M Kelly
(74) *Attorney, Agent, or Firm* — Fox Rothschild LLP

(57) ABSTRACT

This application discloses the compositions comprising biologically active synthetic nanoparticle constructs and methods of use thereof to modify gene expression including transcriptional activation and transcriptional repression.

18 Claims, 19 Drawing Sheets

Figure 1:
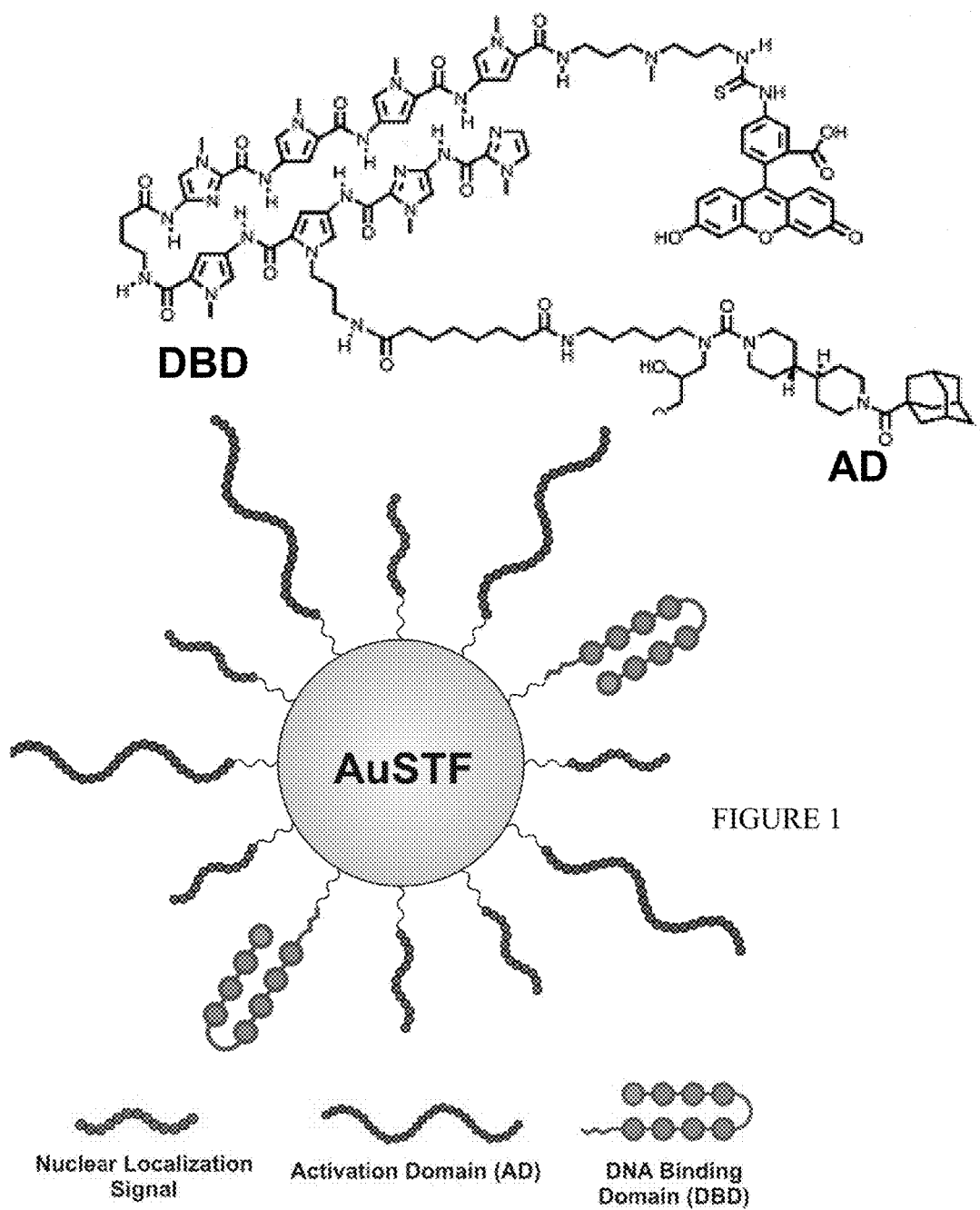

Specification includes a Sequence Listing.

FIGURE 6

SEQUENCE LISTING

<160> NUMBER OF SEQ ID NOS: 39

<210> SEQ ID NO 1
<211> LENGTH: 13
<212> TYPE: PRT
<213> ORGANISM: Human immunodeficiency virus type 1

<400> SEQUENCE: 1

Gly Arg Lys Lys Arg Arg Gln Arg Arg Arg Pro Pro Gln
1               5                   10

<210> SEQ ID NO 2
<211> LENGTH: 16
<212> TYPE: PRT
<213> ORGANISM: Drosophila melanogaster

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 18
<212> TYPE: PRT
<213> ORGANISM: Human immunodeficiency virus type 1

<400> SEQUENCE: 3

Lys Leu Ala Leu Lys Leu Ala Leu Lys Ala Leu Lys Ala Ala Leu Lys
1               5                   10                  15

Leu Ala

<210> SEQ ID NO 4
<211> LENGTH: 6
<212> TYPE: PRT
<213> ORGANISM: Artificial Sequence
<220> FEATURE:
<223> OTHER INFORMATION: chimeric sequence

<400> SEQUENCE: 4

Gly Trp Thr Leu Asn Ser
1               5

<210> SEQ ID NO 5
<211> LENGTH: 21
<212> TYPE: PRT
<213> ORGANISM: Artificial Sequence
<220> FEATURE:
<223> OTHER INFORMATION: chimeric sequence

<400> SEQUENCE: 5

Ala Gly Tyr Leu Leu Gly Lys Ile Asn Leu Lys Ala Leu Ala Ala Leu
1               5                   10                  15

Ala Lys Lys Ile Leu
                20

<210> SEQ ID NO 6
<211> LENGTH: 17
<212> TYPE: PRT
<213> ORGANISM: herpes simplex virus 2

<400> SEQUENCE: 6

Asn Ala Lys Thr Arg Arg His Glu Arg Arg Arg Lys Leu Ala Ile Glu
1               5                   10                  15

Arg

<210> SEQ ID NO 7
<211> LENGTH: 17
<212> TYPE: PRT
<213> ORGANISM: Human immunodeficiency virus type 1

<400> SEQUENCE: 7

Gly Ala Leu Phe Leu Gly Phe Leu Gly Ala Ala Gly Ser Thr Met Gly
1               5                   10                  15

Ala

<210> SEQ ID NO 8
<211> LENGTH: 21
<212> TYPE: PRT
<213> ORGANISM: Artificial Sequence
<220> FEATURE:
<223> OTHER INFORMATION: synthetic sequence

<400> SEQUENCE: 8

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 9
<211> LENGTH: 18
<212> TYPE: PRT
<213> ORGANISM: Mus musculus

<400> SEQUENCE: 9

Leu Leu Ile Ile Leu Arg Arg Arg Ile Arg Lys Gln Ala His Ala His
1               5                   10                  15

Ser Lys

<210> SEQ ID NO 10
<211> LENGTH: 16
<212> TYPE: PRT
<213> ORGANISM: Artificial Sequence
<220> FEATURE:
<223> OTHER INFORMATION: synthetic sequence

<400> SEQUENCE: 10

Tyr Thr Ala Ile Ala Trp Val Lys Ala Phe Ile Arg Lys Leu Arg Lys
1               5                   10                  15

<210> SEQ ID NO 11
<211> LENGTH: 17
<212> TYPE: PRT
<213> ORGANISM: Artificial Sequence
<220> FEATURE:
<223> OTHER INFORMATION: synthetic sequence

<400> SEQUENCE: 11

Ile Ala Trp Val Lys Ala Phe Ile Arg Lys Leu Arg Lys Gly Pro Leu
1               5                   10                  15

Gly

<210> SEQ ID NO 12
<211> LENGTH: 22
<212> TYPE: PRT
<213> ORGANISM: Artificial Sequence
<220> FEATURE:
<223> OTHER INFORMATION: synthetic sequence

<400> SEQUENCE: 12

```
Met Val Thr Val Leu Phe Arg Arg Leu Arg Ile Arg Arg Ala Cys Gly
1               5                   10                  15

Pro Pro Arg Val Arg Val
            20

<210> SEQ ID NO 13
<211> LENGTH: 20
<212> TYPE: PRT
<213> ORGANISM: Artificial Sequence
<220> FEATURE:
<223> OTHER INFORMATION: synthetic sequence

<400> SEQUENCE: 13

Gly Leu Trp Arg Ala Leu Trp Arg Leu Leu Arg Ser Leu Trp Arg Leu
1               5                   10                  15

Leu Trp Arg Ala
            20

<210> SEQ ID NO 14
<211> LENGTH: 29
<212> TYPE: PRT
<213> ORGANISM: Artificial Sequence
<220> FEATURE:
<223> OTHER INFORMATION: synthetic sequence

<400> SEQUENCE: 14

Ser Gly Leu Met Asp Leu Asp Phe Asp Asp Leu Ala Asp Ser Gly Leu
1               5                   10                  15

Met Asp Leu Asp Phe Asp Asp Leu Ala Asp Ser Gly Cys
            20                  25

<210> SEQ ID NO 15
<211> LENGTH: 4
<212> TYPE: PRT
<213> ORGANISM: Drosophila melanogaster

<400> SEQUENCE: 15

Trp Arg Pro Trp
1

<210> SEQ ID NO 16
<211> LENGTH: 19
<212> TYPE: PRT
<213> ORGANISM: Homo sapiens

<400> SEQUENCE: 16

Arg Leu Ile Thr Leu Ala Asp His Ile Cys Gln Ile Ile Thr Gln Asp
1               5                   10                  15

Phe Ala Arg

<210> SEQ ID NO 17
<211> LENGTH: 25
<212> TYPE: PRT
<213> ORGANISM: Artificial Sequence
<220> FEATURE:
<223> OTHER INFORMATION: synthetic sequence

<400> SEQUENCE: 17

Gln Ile Asn Asp Leu Tyr Ser Thr Asp Arg Pro Glu Ser Ala Glu Ala
1               5                   10                  15

Pro Asp Leu Gln Ser Trp Glu Leu Arg
            20                  25
```

<210> SEQ ID NO 18
<211> LENGTH: 27
<212> TYPE: PRT
<213> ORGANISM: Homo sapiens

<400> SEQUENCE: 18

Glu Leu Gln Lys Ser Ile Gly His Lys Pro Glu Pro Thr Glu Glu Trp
1               5                   10                  15

Glu Leu Ile Lys Thr Val Thr Glu Ala His Val
            20                  25

<210> SEQ ID NO 19
<211> LENGTH: 18
<212> TYPE: PRT
<213> ORGANISM: Drosophila melanogaster

<400> SEQUENCE: 19

Ser Thr Pro Ser Ser Lys Thr Lys Asp Leu Gly His Asn Asp Lys Lys
1               5                   10                  15

Ser Ser

<210> SEQ ID NO 20
<211> LENGTH: 29
<212> TYPE: PRT
<213> ORGANISM: Artificial Sequence
<220> FEATURE:
<223> OTHER INFORMATION: synthetic sequence

<400> SEQUENCE: 20

Cys Gly Ser Asp Ala Leu Asp Asp Phe Asp Leu Asp Met Leu Gly Ser
1               5                   10                  15

Asp Ala Leu Asp Asp Phe Asp Leu Asp Met Leu Gly Ser
            20                  25

<210> SEQ ID NO 21
<211> LENGTH: 13
<212> TYPE: PRT
<213> ORGANISM: Simian virus 40

<400> SEQUENCE: 21

Cys Gly Gly Gly Pro Lys Lys Lys Arg Lys Val Glu Asp
1               5                   10

<210> SEQ ID NO 22
<211> LENGTH: 6
<212> TYPE: DNA
<213> ORGANISM: Artificial Sequence
<220> FEATURE:
<223> OTHER INFORMATION: synthetic sequence

<400> SEQUENCE: 22 wgwwww                                                          6

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
cctatgacac gcctttcaaa aga                                      23

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
cagcaccata atcacgatct caa                                              23

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
attcgaaagg acctggagac cc                                               22

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
atcactgcta agcccaatgg c                                                21

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ctgcggaccg aaagaagatg                                                  20

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
atgcagcaac tcaaacagga t                                                21

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
attctcgtca tcgtgtccgc                                                  20

<210> SEQ ID NO 30
<211> LENGTH: 23
<212> TYPE: DNA
<213> ORGANISM: Artificial Sequence
<220> FEATURE:
<223> OTHER INFORMATION: primer

```
<400> SEQUENCE: 30
catccaggaa aggaaatctt gct                                              23

<210> SEQ ID NO 31
<211> LENGTH: 6
<212> TYPE: DNA
<213> ORGANISM: Artificial Sequence
<220> FEATURE:
<223> OTHER INFORMATION: synthetic sequence

<400> SEQUENCE: 31 tgttat                                                                  6

<210> SEQ ID NO 32
<211> LENGTH: 176
<212> TYPE: DNA
<213> ORGANISM: Photinus pyralis

<400> SEQUENCE: 32
gcggtaccgc tagcagctta taacattcca tatgttatac ataacattcc atatgttata      60
cataacattc catatgttat acgtcgacaa gctatgagat ctagactcta gagggtatat     120
aatggaagct cgactccagc ttggcattcc ggtactgttg gtaaaagctt cgaata         176

<210> SEQ ID NO 33
<211> LENGTH: 6
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (3)..(4)
<223> OTHER INFORMATION: n is a, c, g, or t

<400> SEQUENCE: 33 canntg                                                                  6

<210> SEQ ID NO 34
<211> LENGTH: 16
<212> TYPE: PRT
<213> ORGANISM: Human immunodeficiency virus type 1

<400> SEQUENCE: 34

Cys Ala Leu Asn Asn Ala Gly Arg Lys Lys Arg Arg Gln Arg Arg Arg
1               5                   10                  15

<210> SEQ ID NO 35
<211> LENGTH: 5
<212> TYPE: PRT
<213> ORGANISM: Saccharomyces cerevisiae

<400> SEQUENCE: 35

Lys Ile Pro Ile Lys
1               5

<210> SEQ ID NO 36
<211> LENGTH: 7
<212> TYPE: PRT
<213> ORGANISM: Simian virus 40

<400> SEQUENCE: 36

Pro Lys Lys Lys Arg Lys Val
1               5
```

```
<210> SEQ ID NO 37
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (2)..(2)
<223> OTHER INFORMATION: Lys or Arg
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Lys or Arg

<400> SEQUENCE: 37

Lys Xaa Xaa Xaa
1

<210> SEQ ID NO 38
<211> LENGTH: 6
<212> TYPE: DNA
<213> ORGANISM: Artificial Sequence
<220> FEATURE:
<223> OTHER INFORMATION: synthetic sequence

<400> SEQUENCE: 38 ggtacc                                                                  6

<210> SEQ ID NO 39
<211> LENGTH: 6
<212> TYPE: DNA
<213> ORGANISM: Artificial Sequence
<220> FEATURE:
<223> OTHER INFORMATION: synthetic sequence

<400> SEQUENCE: 39 aagctt                                                                  6
```

BIOLOGICALLY ACTIVE SYNTHETIC NANOPARTICLE CONSTRUCTS AND METHODS OF USE THEREOF

CROSS REFERENCE TO RELATED APPLICATIONS

This application is the U.S. National Phase of International Patent Application Serial No. PCT/US2014/052569 filed Aug. 25, 2014 which claims the benefit of priority under 35 U.S.C. § 119(e) of U.S. Provisional Application No. 61/869,284 filed Aug. 23, 2013 and U.S. Provisional Application No. 61/947,898 filed Mar. 4, 2014. The disclosures of the applications are incorporated herein by reference in their entireties.

STATEMENT REGARDING FEDERALLY SPONSORED RESEARCH

The invention described herein was supported in whole or in part by grants from the National Institutes of Health (New Innovator Award No. NIH-1DP20D006462-01). The U.S. Government has certain rights in this invention.

FIELD OF THE INVENTION

This invention relates to biologically active synthetic nanoparticle construct compositions and methods of their use in regulating, mediating, or modifying biological activity and processes including gene expression and the cellular processes that rely on gene expression such as stem cell differentiation.

BACKGROUND OF THE INVENTION

Cellular biology comprises a wide range of study involving a broad set of cellular processes. These processes include, but are not necessarily limited to, cellular growth, maintenance, metabolism, proliferation, differentiation, migration, as well as inter- and intracellular signaling pathways. These cellular processes are mediated by a wide variety of endogenous proteins and other ligands, for example hormones and other steroids. While these cellular processes are incredibly varied, the regulation of these cellular processes can ultimately be traced back to regulation of gene expression, and most commonly, but not necessarily, regulation of gene expression at the transcriptional level.

Gene expression is the process wherein the information contained in a particular gene is ultimately manifested in a protein, the mechanism of which is explained by the Central Dogma Theory (CDT). The CDT, first proposed by Francis Crick in 1956, is often considered the fundamental unifying theory of the life sciences and it states that the flow of genetic information, under ordinary conditions, goes from DNA to RNA via transcription, and then from RNA to protein via translation. Since then, scientists have discovered several processes that are exceptions, notably for example that of reverse transcription such as that undertaken by retroviruses, as well as several processes that are not explicitly covered in the CDT, such as forms of posttranslational modifications.

Gene expression is most commonly regulated at the transcriptional level and involves the alteration of transcription rates within a cell. Transcriptional regulation may include either transcriptional activation or transcriptional repression. Transcription of a gene requires the presence of RNA polymerase (RNAP) to proceed. RNAP can initiate transcription at specific DNA sequences known as promoters. Promoters are non-coding DNA sequences which are found near to and upstream of genes. Transcriptional regulation often involves the use of transcription factors (TFs), which are compounds that can bind to specific DNA sequences. TFs can function as an activator and thus promote transcription, or a repressor, and thus block transcription. Activators bind to DNA regions known as enhancers, and enhance the interactions between RNAP and promoters, thus increasing the rate of transcription. Repressors bind to DNA regions known as silencers, which are often located upstream of the target gene and near the promoter region. Repressors function to prevent the binding of RNAP to promoters and thus prevent transcription.

TFs that function as activators are comprised of two fundamental domains that function synergistically to activate gene expression: the DNA-binding domain (DBD) and the activation domain (AD). The DBD targets and binds to specific enhancer DNA sequences while the AD recruits proteins and RNAP to initiate and sustain transcription. TFs that function as repressors are likewise comprised of a DBD that similarly targets and binds to specific silencer DNA sequences. TFs that function as repressors may also be comprised of a repression domain (RD) are comprised of non-DNA binding proteins called corepressors. In eukaryotes, corepressors are proteins that bind to certain repressors in order to activate them, so that the repressor can bind to the silencer region and block transcription.

The field of nanotechnology has recently made great strides in contributing to therapeutic applications ranging from molecular imaging, stem cell differentiation, and drug delivery. There have been past attempts to create synthetic analogues of TFs for use in a wide variety of therapeutic applications. These synthetic analogues are called synthetic transcription factors (STFs). Further like endogenous TFs, STFs may act as either activators or repressors. Like TFs, STFs contain a DBD and either an AD if functioning as an activator and optionally an RD if functioning as a repressor. Activator STFs have been developed in the past by combining a DBD moiety such as zinc finger, oligonucleotides, and hairpin polyamide to an AD moiety such as wrenchnolol, peptoids, and peptides to induce gene expression. Repressor STFs have been developed in the past by combining a DBD moiety with RD moieties to repress gene expression.

STFs have a high binding affinity for DNA, they can exhibit specificity to bind to only certain sites such as enhancers or silencers, for example via tunable hairpin polyamides that complement targeted DNA sequences, and they possess a small molecular size. As such, STFs have significant potential therapeutic application. However, existing STFs suffer from a number of known problems that currently limit their potential therapeutic applications. STFs are known to have poor penetration of the nuclear membrane, which is significant because transcription occurs in the nucleus. STFs that cannot easily penetrate the nuclear membrane cannot effectively regulate transcription. Furthermore, STFs are often subject to intracellular degradation, thus limiting their effectiveness. Surprisingly, the current invention relating to biologically active synthetic nanoparticle constructs overcomes these limitations and provides effective compositions for use in regulating, mediating, or modifying biological activity and processes including gene expression and the cellular processes that rely on gene expression such as cellular proliferation, differentiation, and migration.

SUMMARY OF THE INVENTION

The invention described herein involves biologically active synthetic nanoparticle constructs and methods of use of the biologically active synthetic nanoparticle constructs.

Some embodiments of this invention comprises biologically active synthetic nanoparticle constructs comprised of a biologically inert substrate, a plurality of DBD domains, and a plurality of NLS domains. These embodiments may further comprise a plurality of AD domains, a plurality of RD domains, or other various domains. These domains are attached to the surface of the biologically inert substrate.

Other embodiments of this invention comprises use of the biologically active synthetic nanoparticle constructs to activate transcription. The biologically inert substrates in these embodiments are comprised of a biologically inert substrate, a plurality of DBD domains, a plurality of NLS domains, a plurality of AD domains, and may further comprise other various domains. These domains are attached to the surface of the biologically inert substrate.

Other embodiments of this invention comprises use of the biologically active synthetic nanoparticle constructs to repress transcription. The biologically inert substrates in these embodiments are comprised of a biologically inert substrate, a plurality of DBD domains, a plurality of NLS domains, and may further comprise a plurality of RD domains, and may further comprise other various domains. These domains are attached to the surface of the biologically inert substrate.

Further embodiments of this invention comprises use of the biologically active synthetic nanoparticle constructs to modulate or regulate stem cell differentiation. The biologically inert substrates in these embodiments biologically active synthetic nanoparticle constructs comprised of a biologically inert substrate, a plurality of DBD domains, and a plurality of NLS domains. These embodiment may further comprise a plurality of AD domains, a plurality of RD domains, or other various domains. These domains are attached to the surface of the biologically inert substrate.

Further embodiments of this invention comprise a medical device for delivery of the biologically active synthetic nanoparticle constructs into an organism. Yet further embodiments involve methods of use for the medical devices.

FIGURES

FIG. 1: Schematic Depiction of a Biologically Active Synthetic Nanoparticle Construct. This example of a biologically active synthetic nanoparticle construct is comprised of a biologically inert substrate, a plurality of DBD, a plurality of NLS, and an optional plurality of AD, which are attached to the surface of the biologically inert substrate. The presence of the AD, NLS, and DBD allows this example of a biologically active synthetic nanoparticle construct to activate transcription of a target gene.

Figure 2:
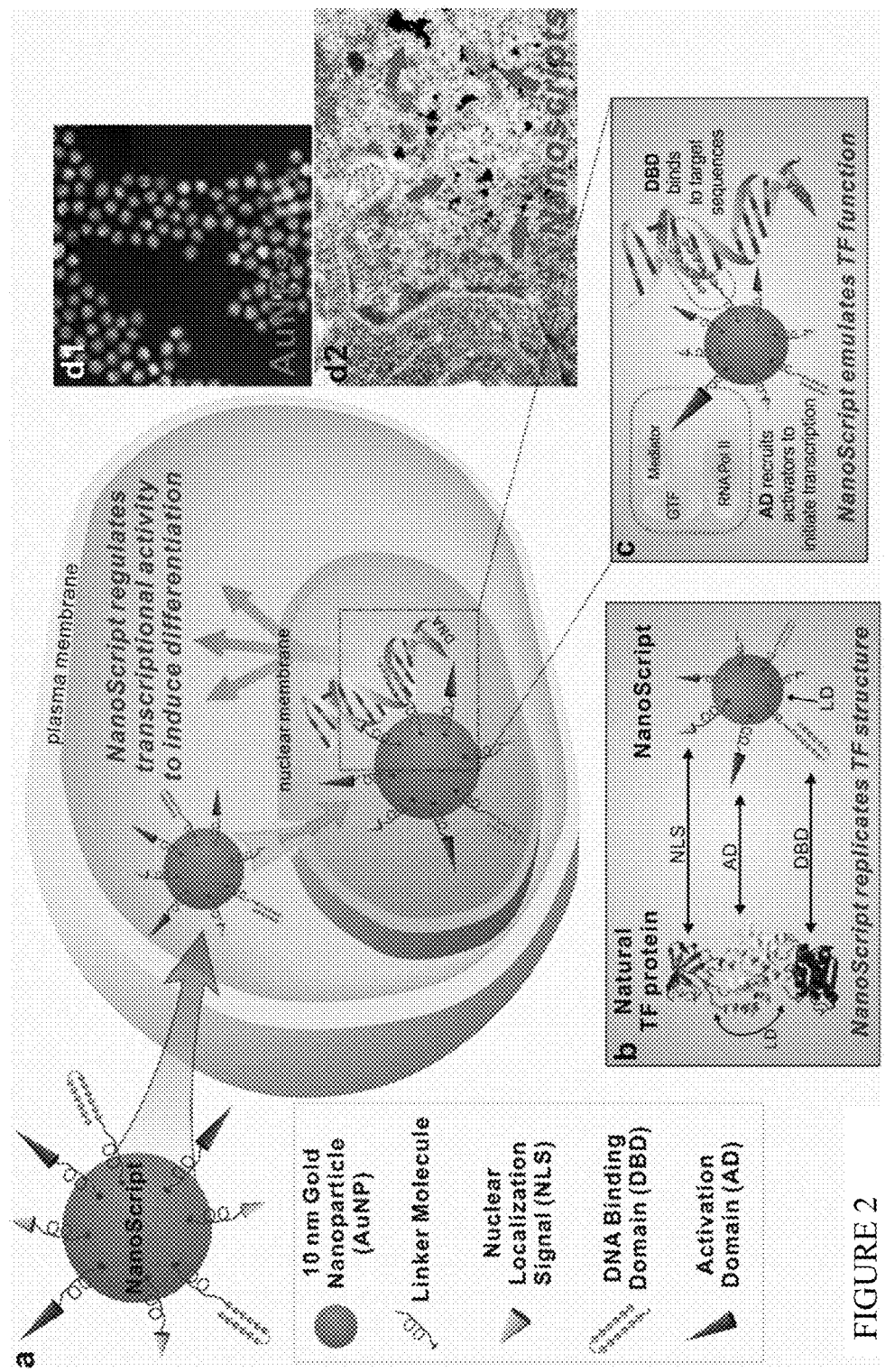

FIG. 2: Schematic Representation and Characterization of Biologically Active Synthetic Nanoparticle Construct Design and Function. (a) This biologically active synthetic nanoparticle construct was designed by assembling the DBD, AD, and NLS, onto a single 10 nm gold nanoparticle. This platform may replicate the structure and function of TFs. This construct penetrates the cell membrane and enters the nucleus through the nuclear receptor with help of the NLS peptide. Once in the nucleus, the construct interacts with DNA to initiate transcriptional activity and induce gene expression. (b) When comparing the structure of this biologically active synthetic nanoparticle construct to representative TF proteins, the three essential domains are effectively replicated. The linker molecule fuses the multi-domain protein together and is replicated by the gold nanoparticle. (c) The DBD binds to complementary DNA sequences while the AD recruits transcriptional machinery components such as RNA polymerase II (RNAP II), mediator complex, and general transcription factors (GTFs). The synergistic function of the DBD and AD moieties on the construct initiates transcriptional activity and expression of targeted genes. (d) The gold nanoparticles are monodisperse and uniform. The constructs are shown to effectively localize within the nucleus, which is important because transcriptional activity occurs only in the nucleus.

Figure 3:
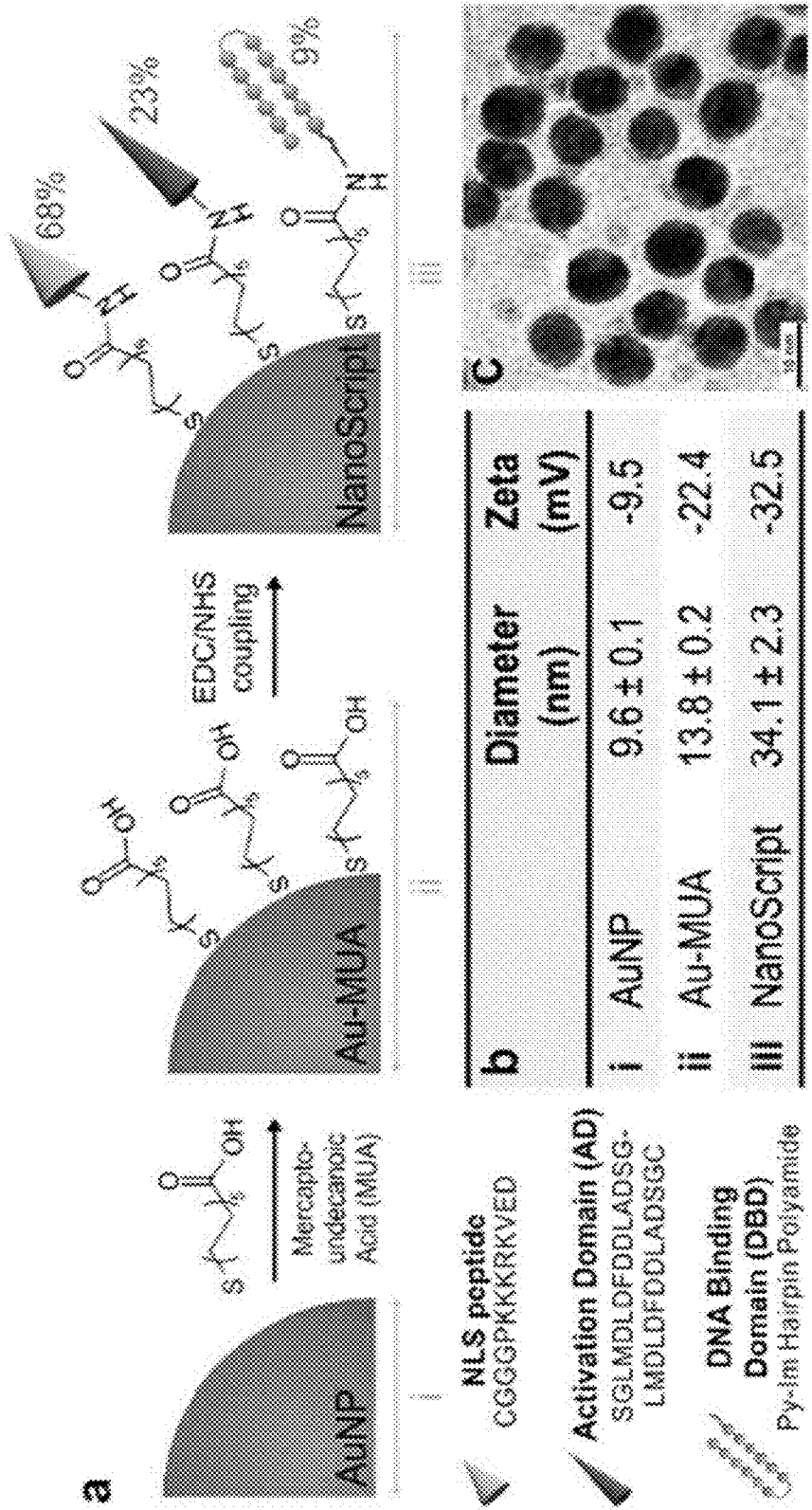

FIG. 3: Construction and Characterization of Biologically Active Synthetic Nanoparticle Construct. 10 nm AuNPs are first coated with mercaptoundecanoic acid (MUA), then activated with EDC/NHS coupling chemistry, and finally the small molecules components are assembled to create the biologically active synthetic nanoparticle construct. This reaction was carried out in a controlled buffered (pH=6.0-7.4) solution to ensure conjugation through the primary amine, but there is a possibility that NLS binds either directly to the AuNP or through lysine side chains, which should not influence its functionality. (b) The hydrodynamic diameter of the constructs increases stepwise with the conjugation of functional components. The surface charge of the constructs also increases stepwise with the addition of more negatively charged components. (c) A TEM micrograph showing a monodisperse and uniform distribution of the construct.

Figure 4:
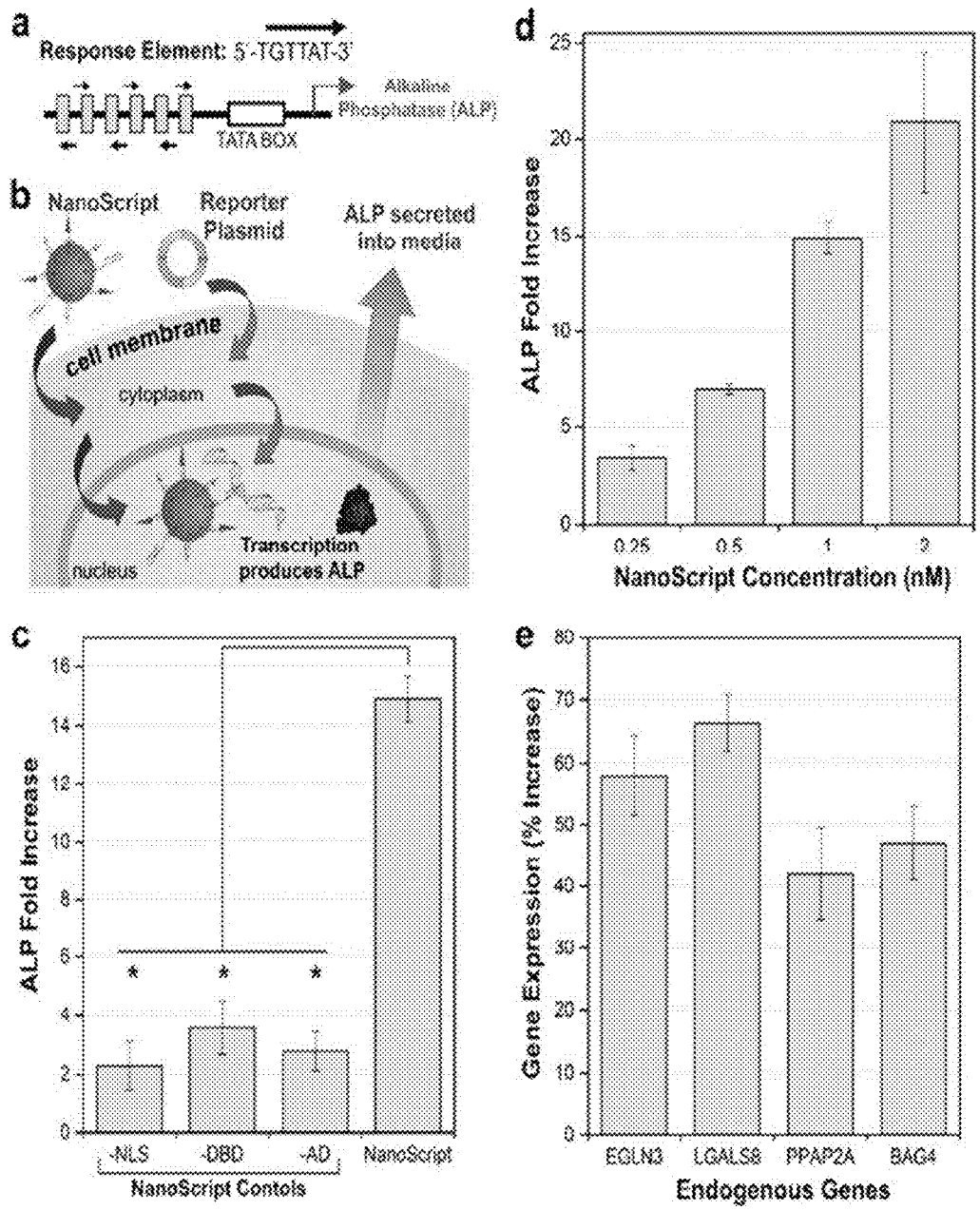

FIG. 4: Transcription of Reporter Gene Induced by Biologically Active Synthetic Nanoparticle Construct. (a) The reporter gene containing 6 copies of the response element is located upstream from the TATA Box and secretes alkaline phosphatase (ALP) upon transcription. (b) Schematic representation of co-delivering the reporter plasmid and the biologically active synthetic nanoparticle construct. After the construct and the reporter plasmid both localize within the nucleus, transcriptional activity is initiated to produce ALP, which is secreted into the culture media. (c) The ALP fold induction initiated by the construct (1 nM) compared to controls which lack individual components (d) Concentration-dependent induction of ALP by the construct. (e) HeLa cells were incubated with the construct (1 nM) and 48 hours later, qPCR analysis reveals activation of targeted genes. Standard error, mean, and t-test analysis for all experiments was derived from three individual trials. ALP was measured 48 hr posttransfection and fold increase is relative to unmodified AuNP controls. T-test analysis * for P<0.01.

Figure 5:
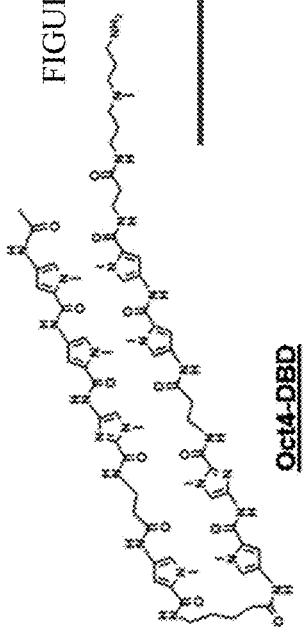
Figure 5:
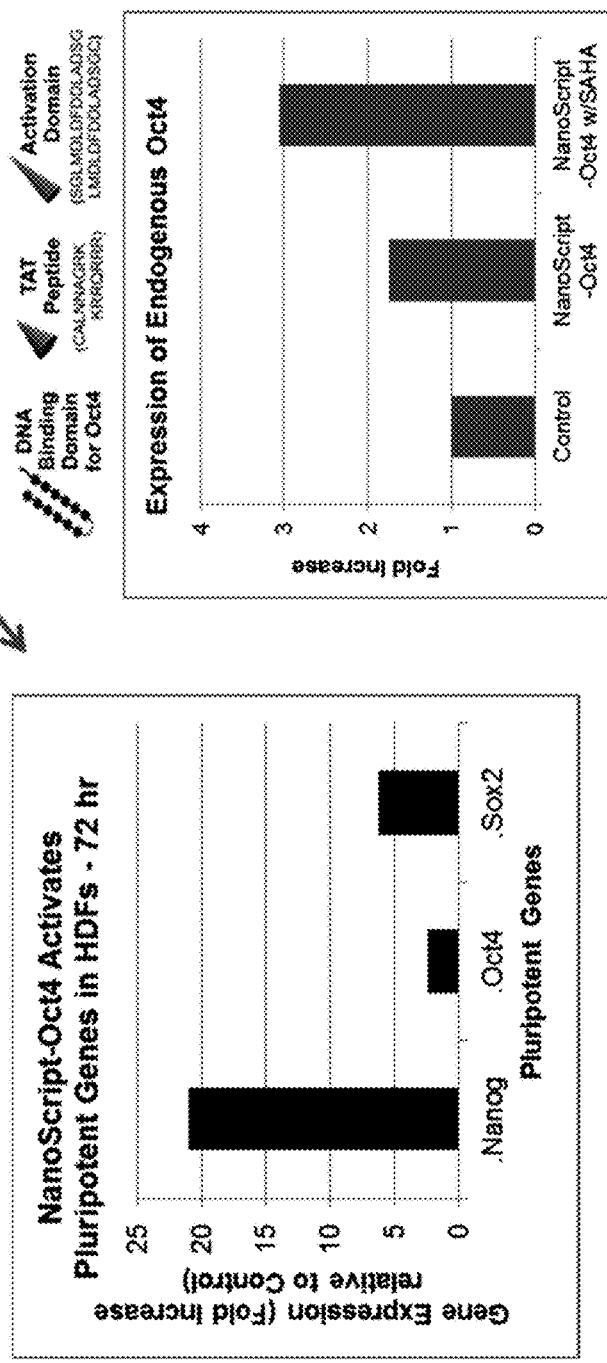

FIG. 5: Inducing Expression of Reprogramming Pluripotent Genes. The biologically active synthetic nanoparticle construct activates the Oct4 gene and other pluripotency genes in the human dermal fibroblasts.

Figure 6:
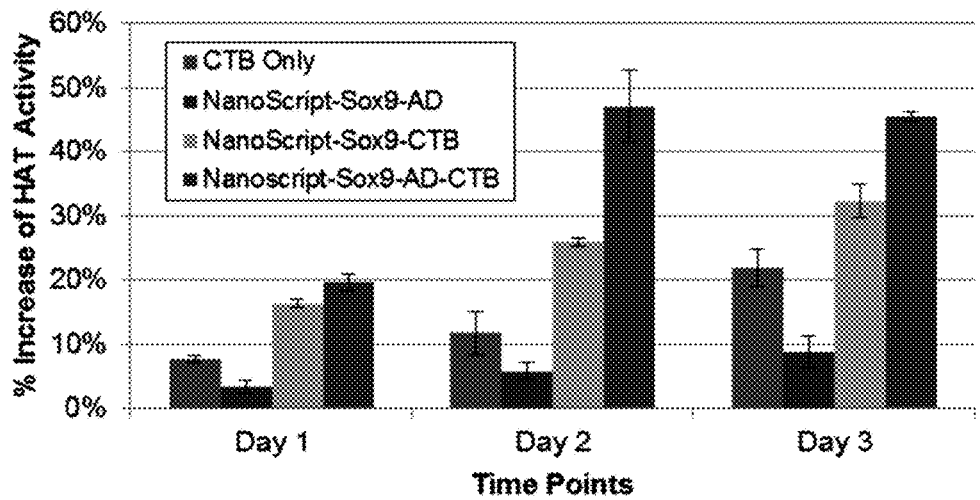
Figure 6:
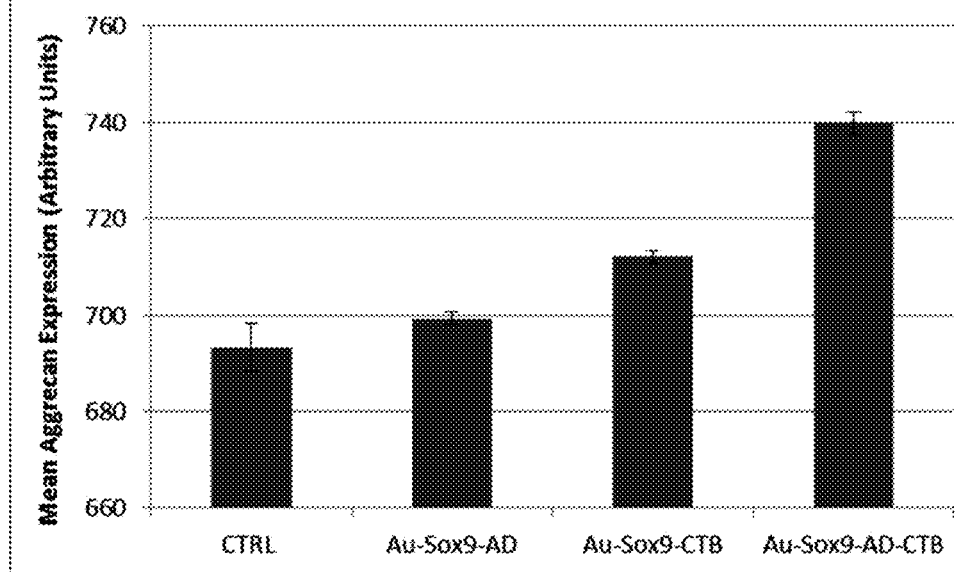

FIG. 6: Modification of Biologically Active Synthetic Nanoparticle Constructs with CTB Accelerates Chondrocyte Differentiation. Biologically active synthetic nanoparticle constructs modified with CTB for increased HAT activity. By supplementing the construct with CTB, it more closely mimics the structure of TF proteins. The CTB [N-(4-Chloro-3-trifluoromethyl)-2-ethoxy-6-pentadecylbenzamide] molecule structure is shown. The potency of the CTB molecule and the CTB molecule conjugated on the gold nanoparticle (AuNP) was tested by quantifying HAT (Histone acetyltransferase) activity. The expression of Aggrecan, a distinct chondrogenic marker, was evaluated 7 days post transfection.

Figure 7:
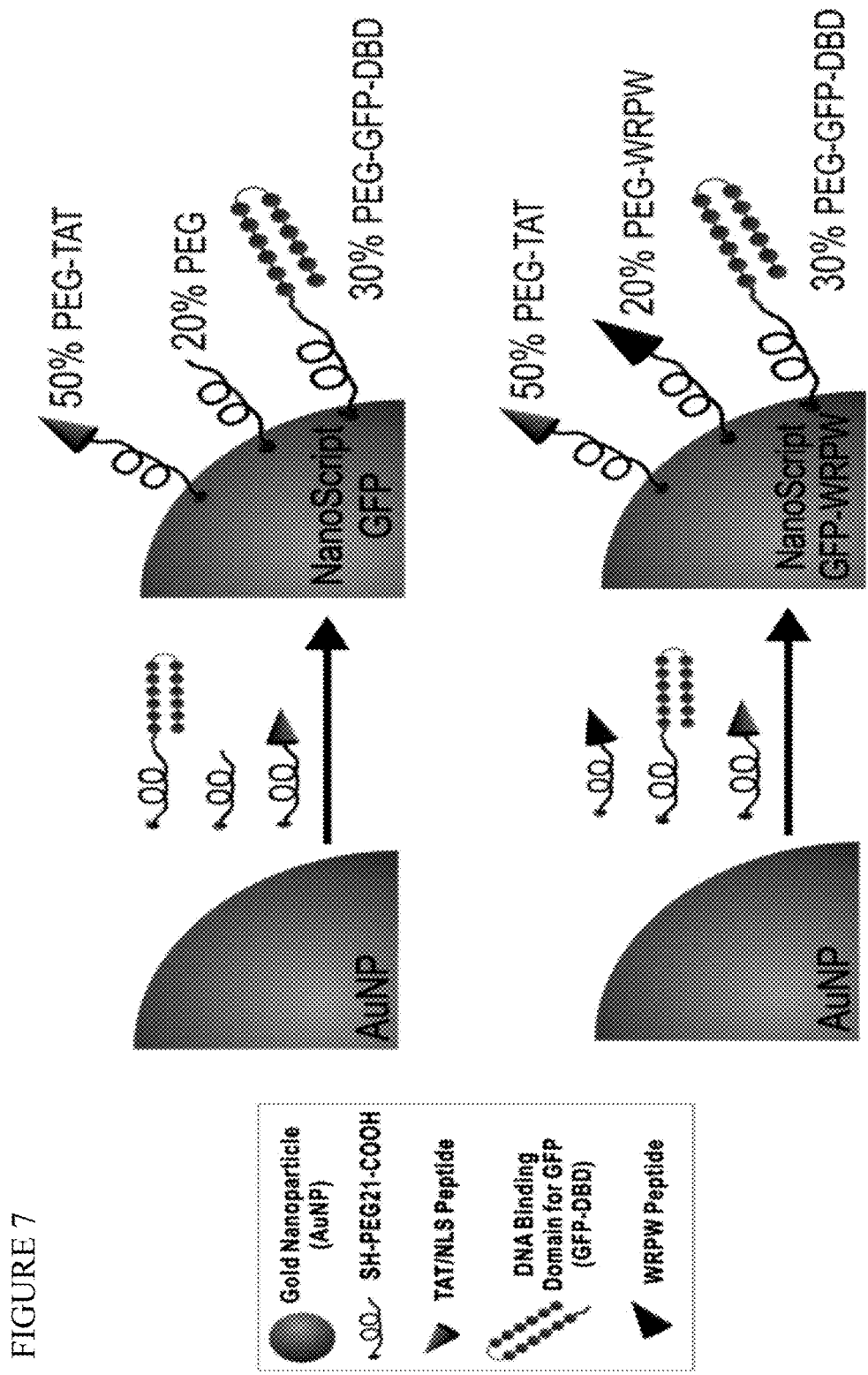
Figure 7:
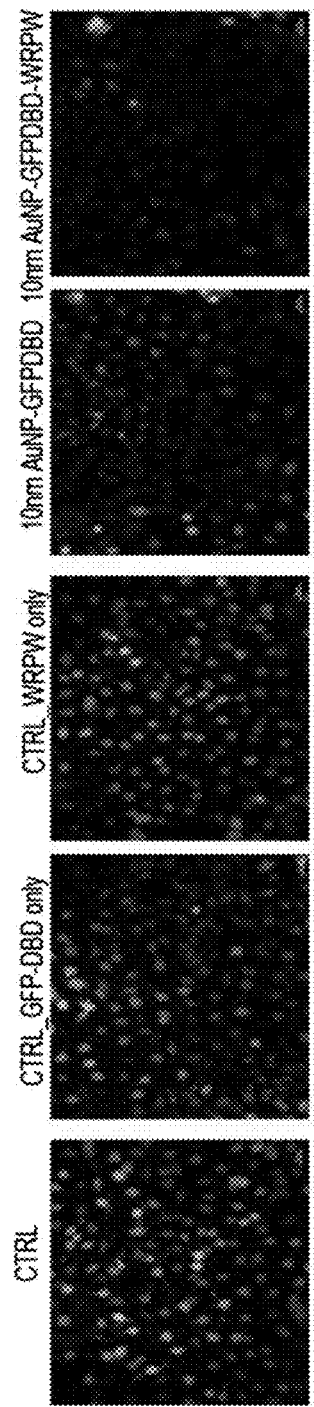
Figure 7:
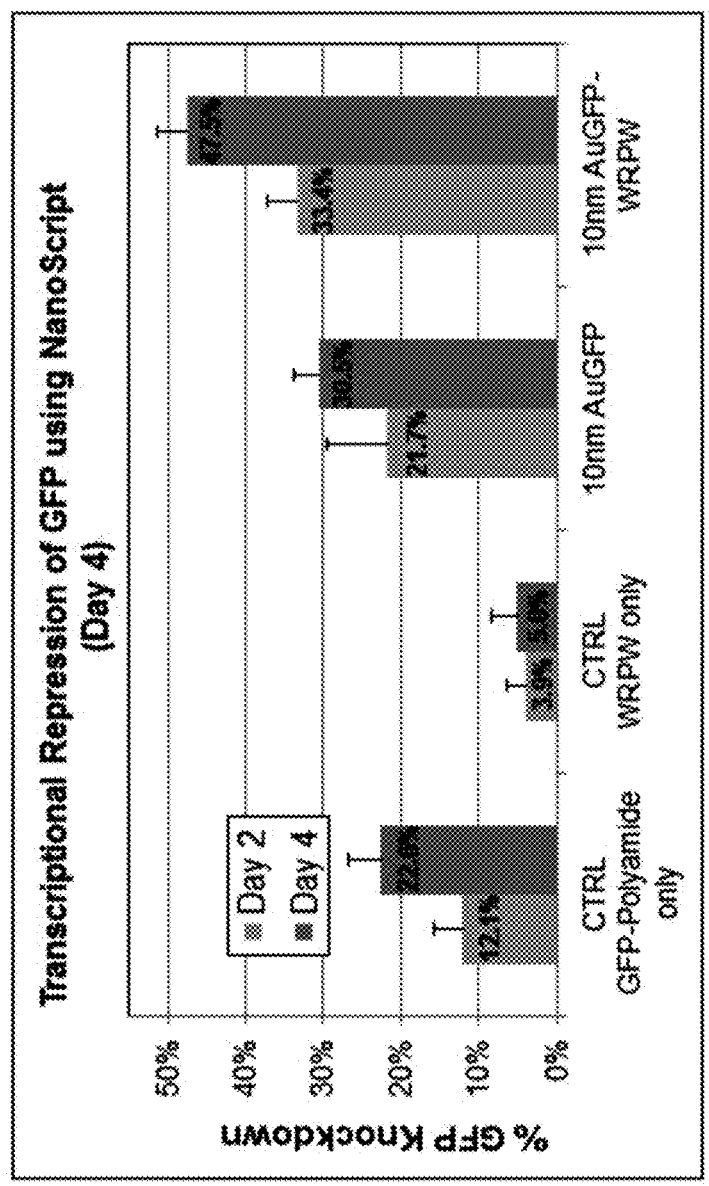

FIG. 7: Transcriptional Repression of GFP Reporter using Biologically Active Synthetic Nanoparticle Constructs. When the biologically active synthetic nanoparticle constructors were transfected into GFP-labeled rat neural stem cells (rNSCs), an obvious trend of decreased GFP signal was observed. After 48 hours, those rates infected with the constructs showed the greatest repression of the GFP by almost 48%.

Figure 8:
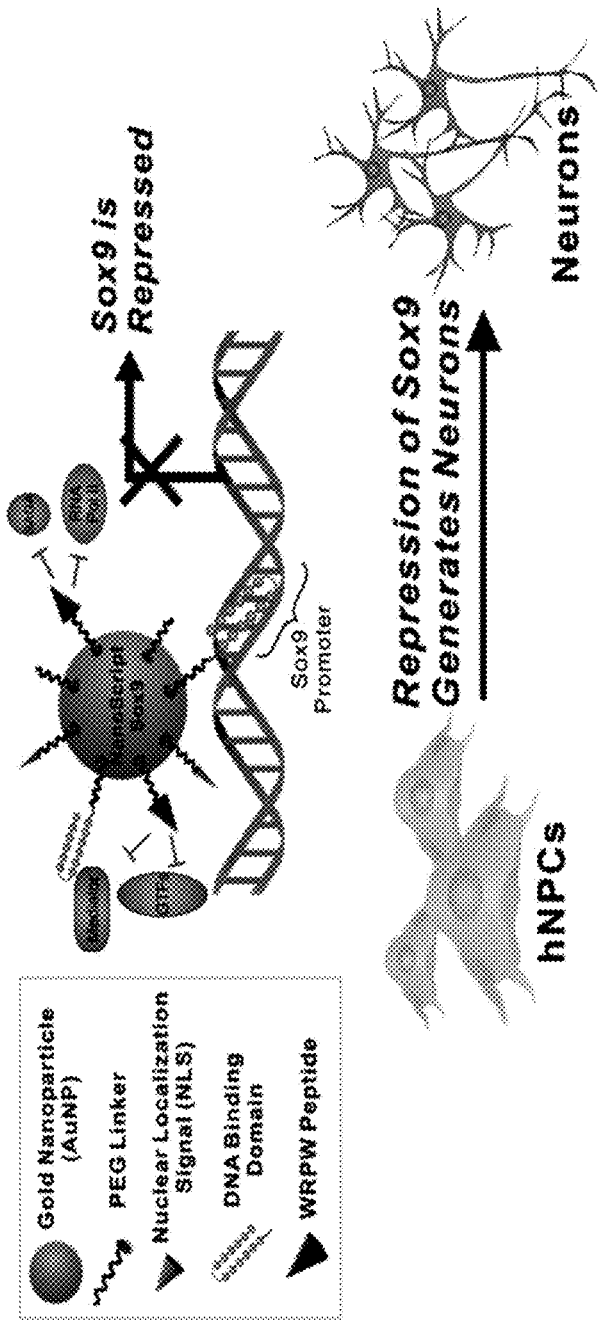

FIG. 8: Schematic Representation of Repression of Sox9 by Biologically Active Synthetic Nanoparticle Constructs. Endogenous genes are transcribed when the transcriptional basal machinery (comprising of GTFs, RNA Poly II, SAGA, Mediators, etc.) are recruited to a target sequence, such as Sox9, and initiates transcription. But, when the biologically active synthetic nanoparticle constructs are added, the hairpin polyamide sterically blocks transcription while the WRPW-corepressor inhibits recruitment of the transcriptional basal machinery. Thus Sox9 transcription is repressed. In human neural progenitor cells (hNPCs), if the Sox9 gene is repressed, generation of neurons occurs at an enhanced rate.

Figure 9:
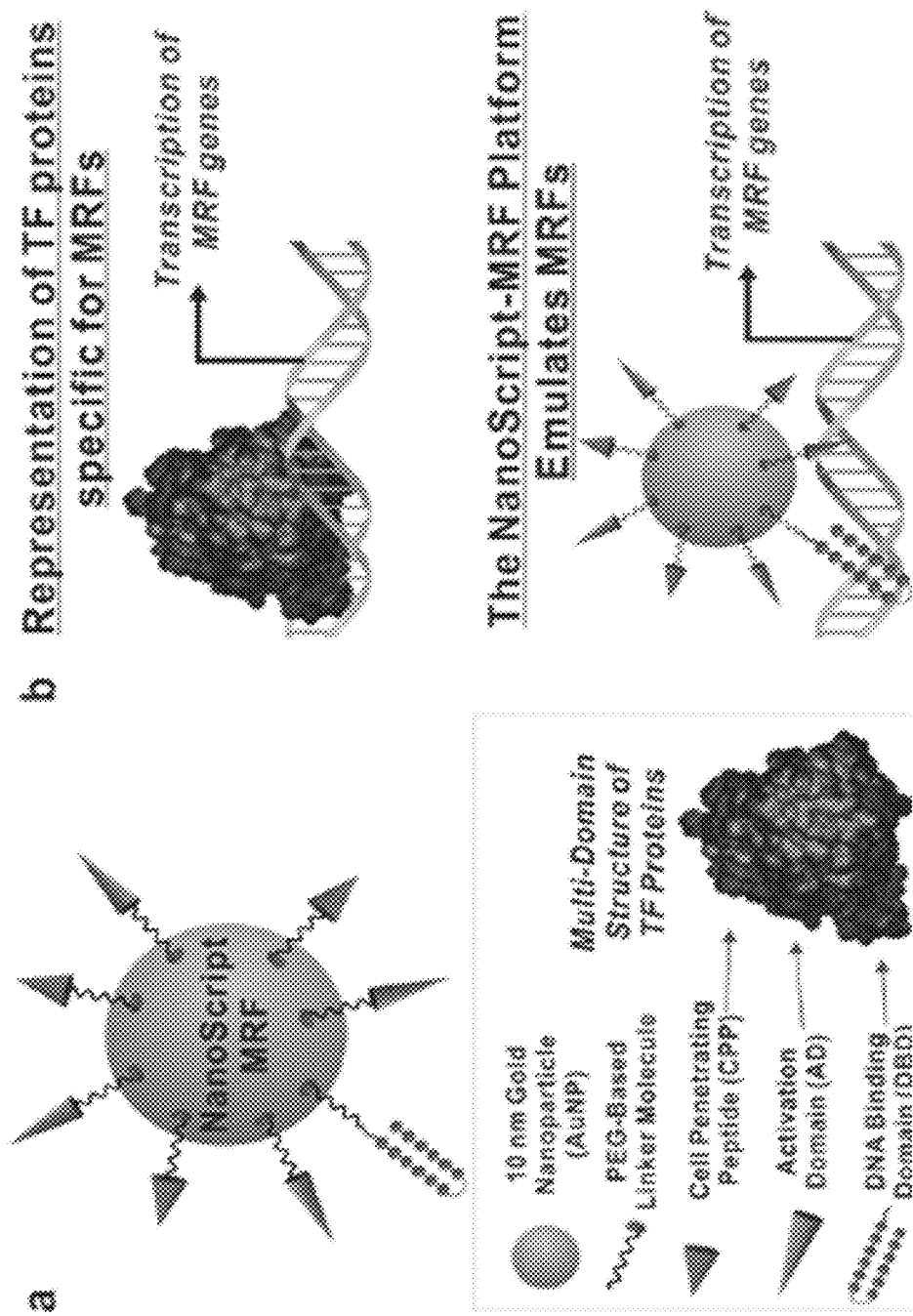
Figure 9:
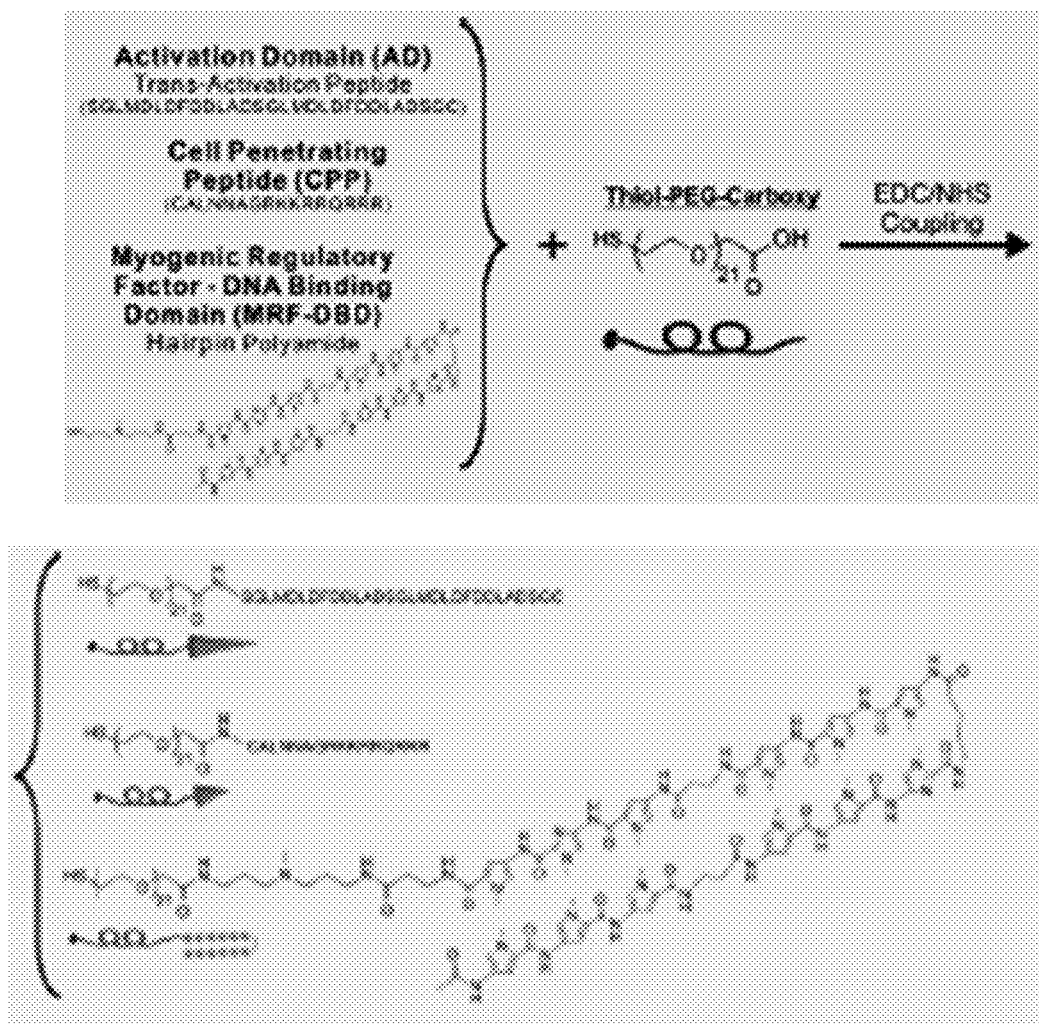
Figure 9:
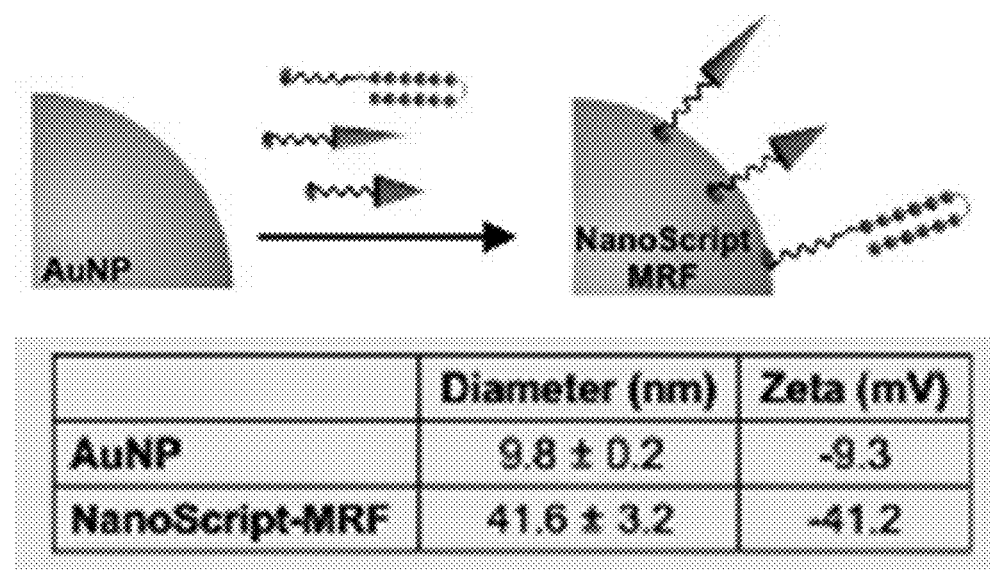

FIG. 9: Schematic Representation and Conjugation of Biologically Active Synthetic Nanoparticle Constructs with MRF Domains. (a) The multi-domain structure of TF, such as the NLS, AD, DBD domains, are emulated through small molecules and peptide counterparts conjugated on inert substrates. By assembling these specific biomolecules on inert substrates such as AuNPs, the biologically active synthetic nanoparticle construct is created. (b) The myogenic regulatory factors (MRFs), which regulate muscle cell differentiation, are TFs that interact with DNA to regulate gene expression for muscle-specific genes. The biologically active synthetic nanoparticle construct is capable of mimicking endogenous MRFs and can perform the same function of regulating muscle-specific genes, which can lead to subsequent stem cell differentiation. (c) The amine terminus on each domain (AD, NLS, and DBD) was conjugated to the thiol-PEG-carboxy linker molecule via EDC/NHS coupling. (d) The domains were assembled on AuNPs via the thiol moieties to construct the biologically active synthetic nanoparticle construct, and (e) characterization confirmed the diameter and surface charge of the construct.

Figure 10:
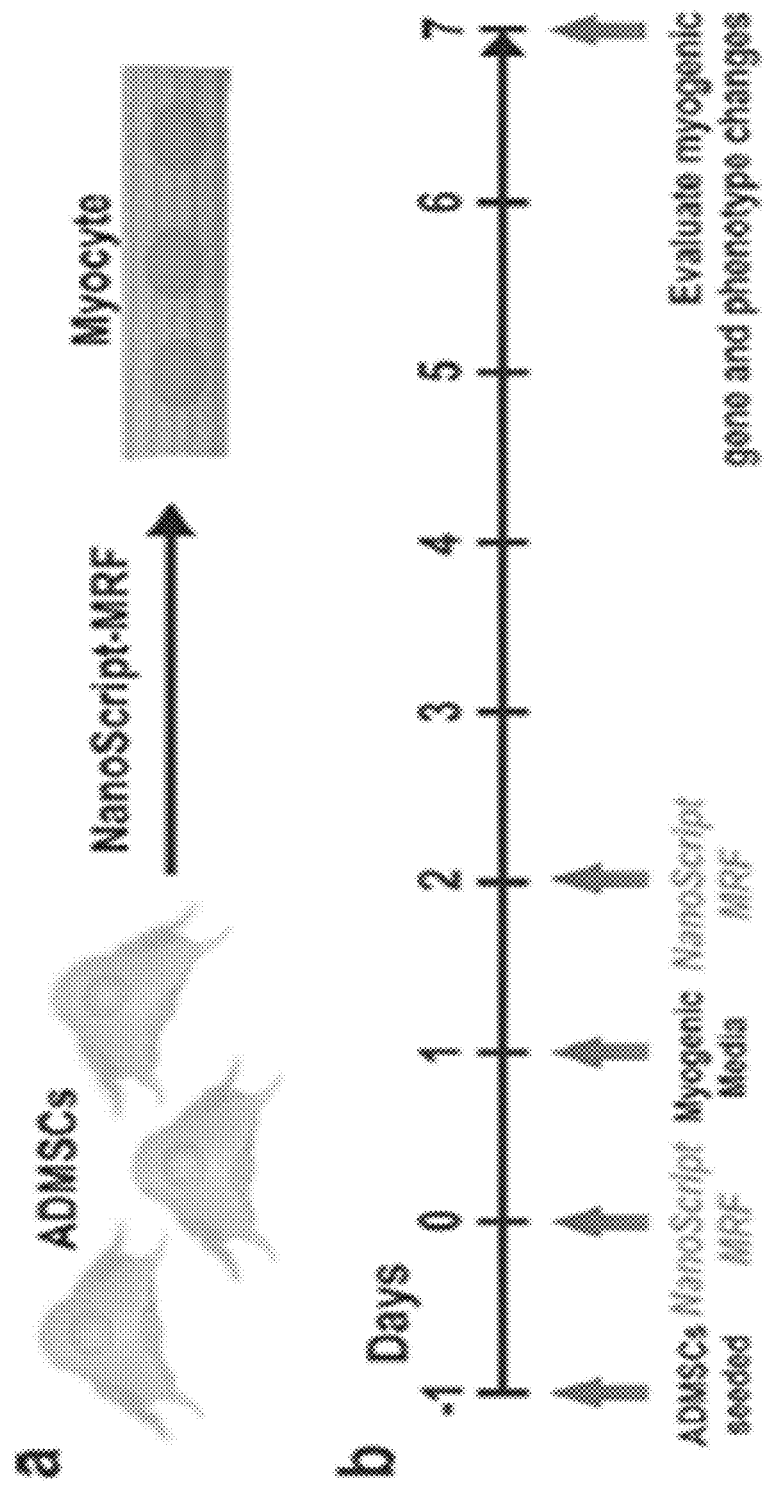
Figure 10:
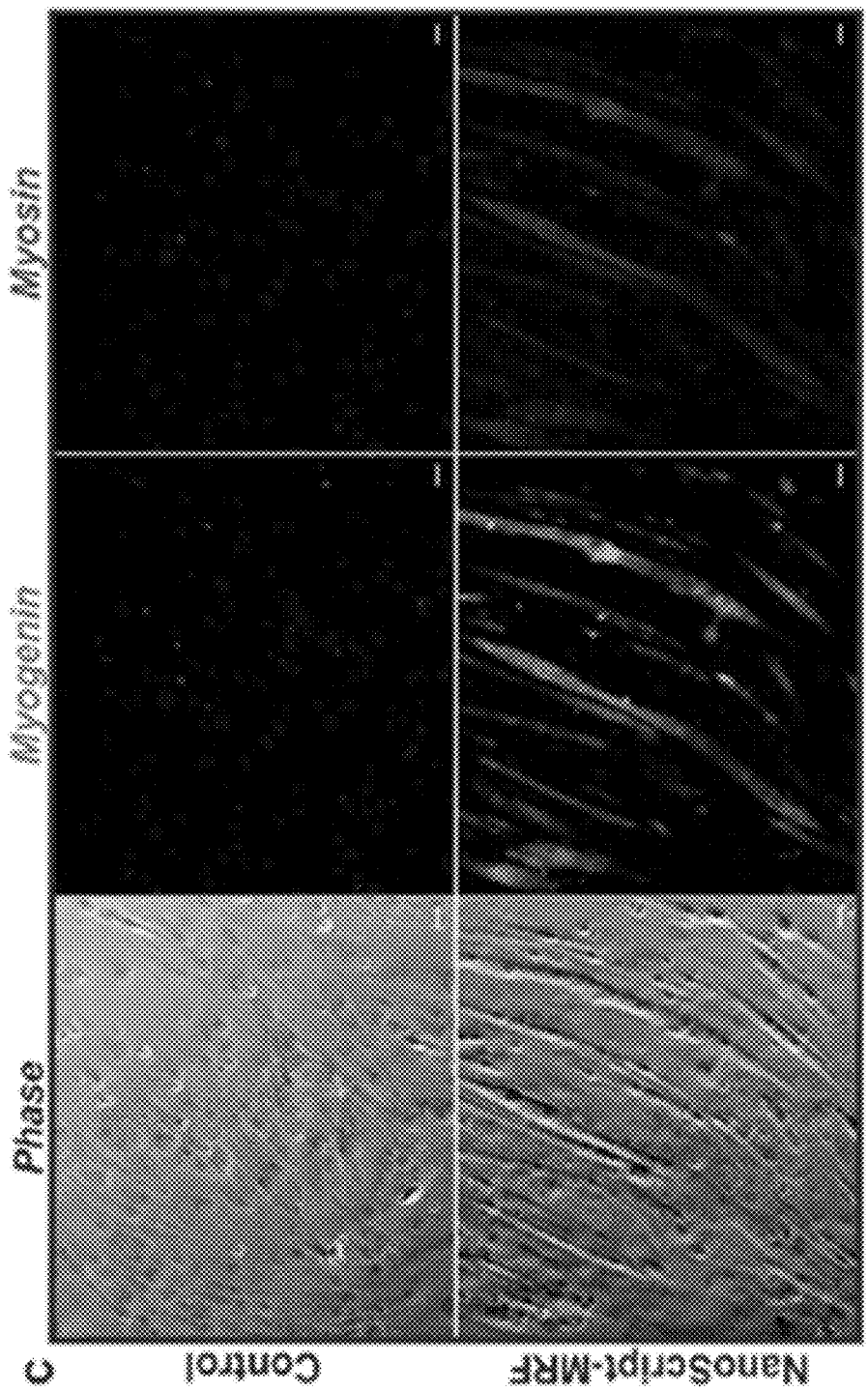
Figure 10:
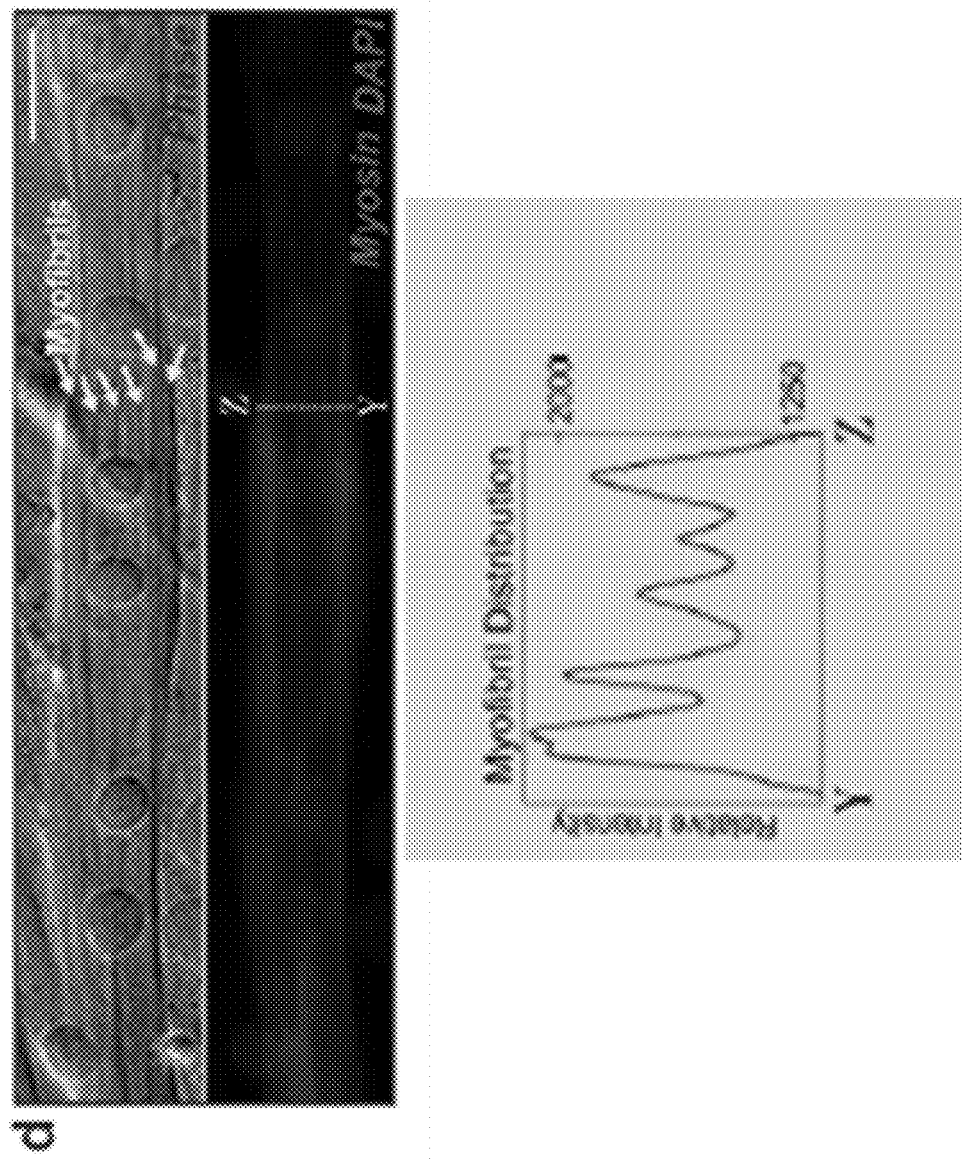

FIG. 10: Biologically Active Synthetic Nanoparticle Constructs Generate Myocytes After 7 Days. Schematic representation of ADMSCs differentiating into myocyte muscle cells after treatment with biologically active synthetic nanoparticle constructs with MRF domains. (b) Differentiation timeline of ADMSCs being treated with the nanoparticle constructs. (c) Phase and fluorescence images of ADMSCs that were fixed and stained on Day 7. The untreated control ADMSCs (top row) and the constructs treated ADMSCs (bottom row) were stained for muscle-specific markers such as myogenin (green, middle column) and myosin (red, right column), and the nucleus marker DAPI (blue). (d) Magnified phase and fluorescence image of multi-nucleated myocytes that have developed actin/myosin filaments called myofibrils (indicated with white arrows). A fluorescence intensity profile of the induced myocytes shows the distribution of six distinct peaks for each individual myofibril (Scalebar=20 µm).

Figure 11:
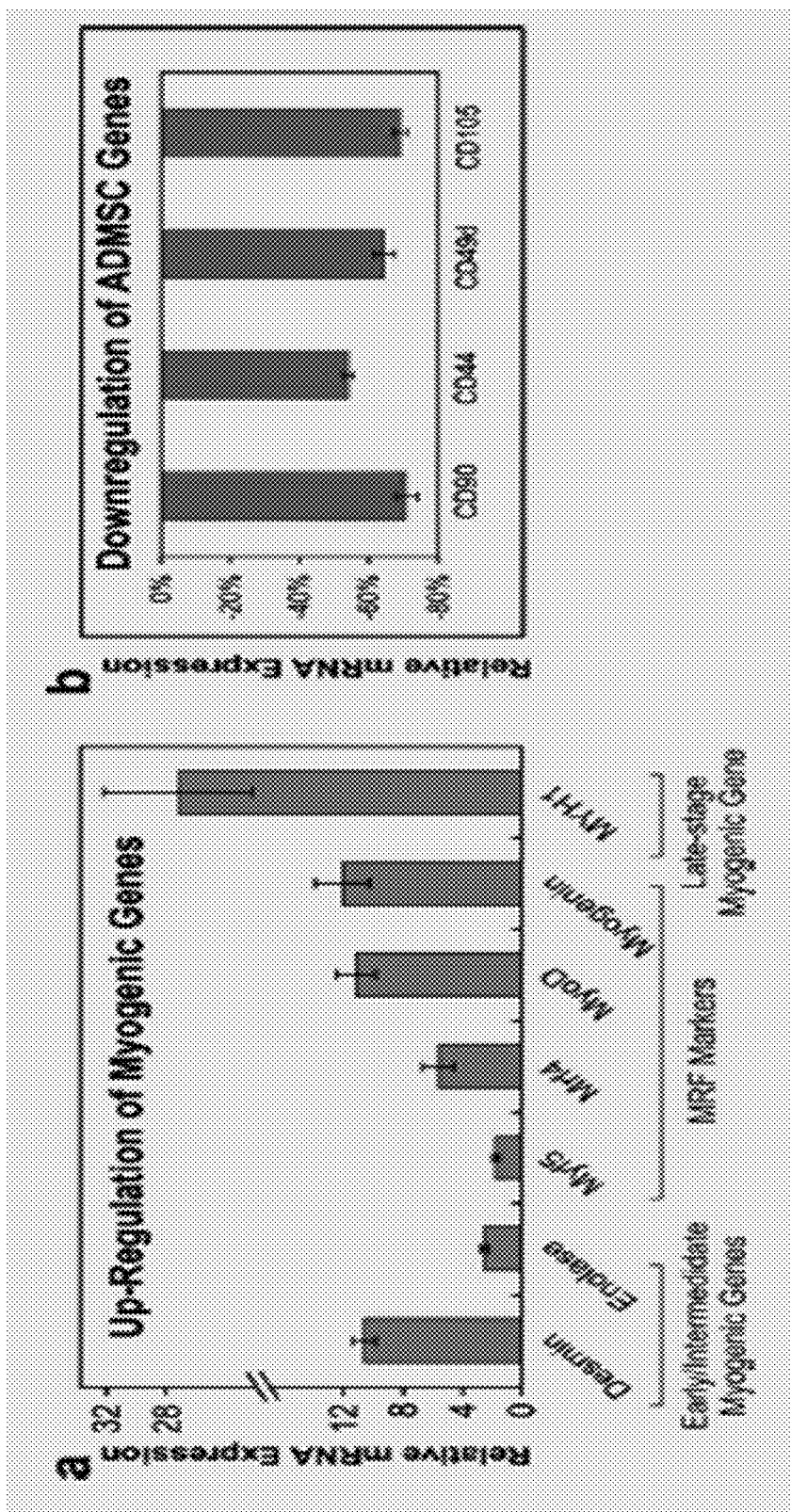
Figure 11:
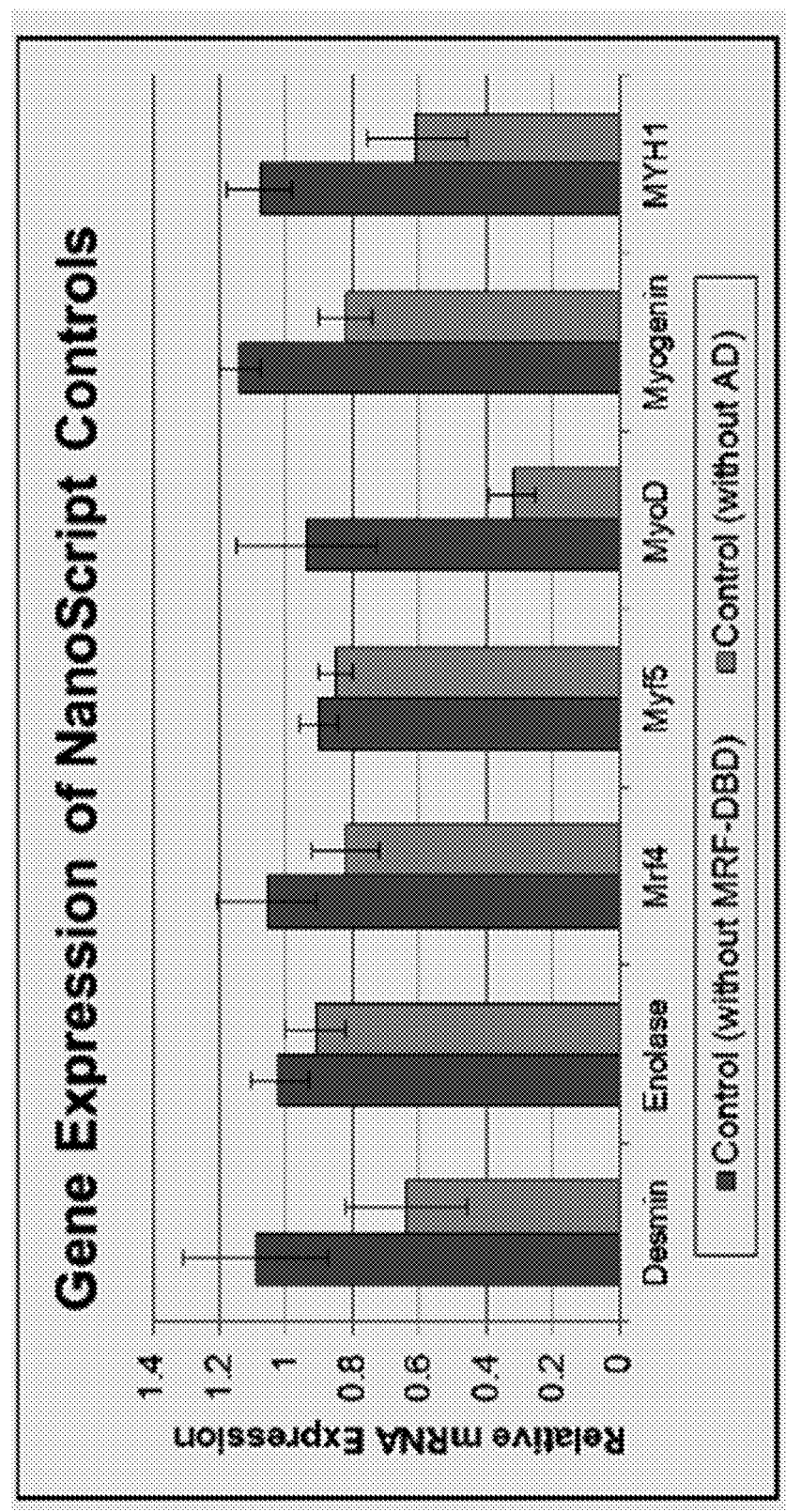
Figure 11:
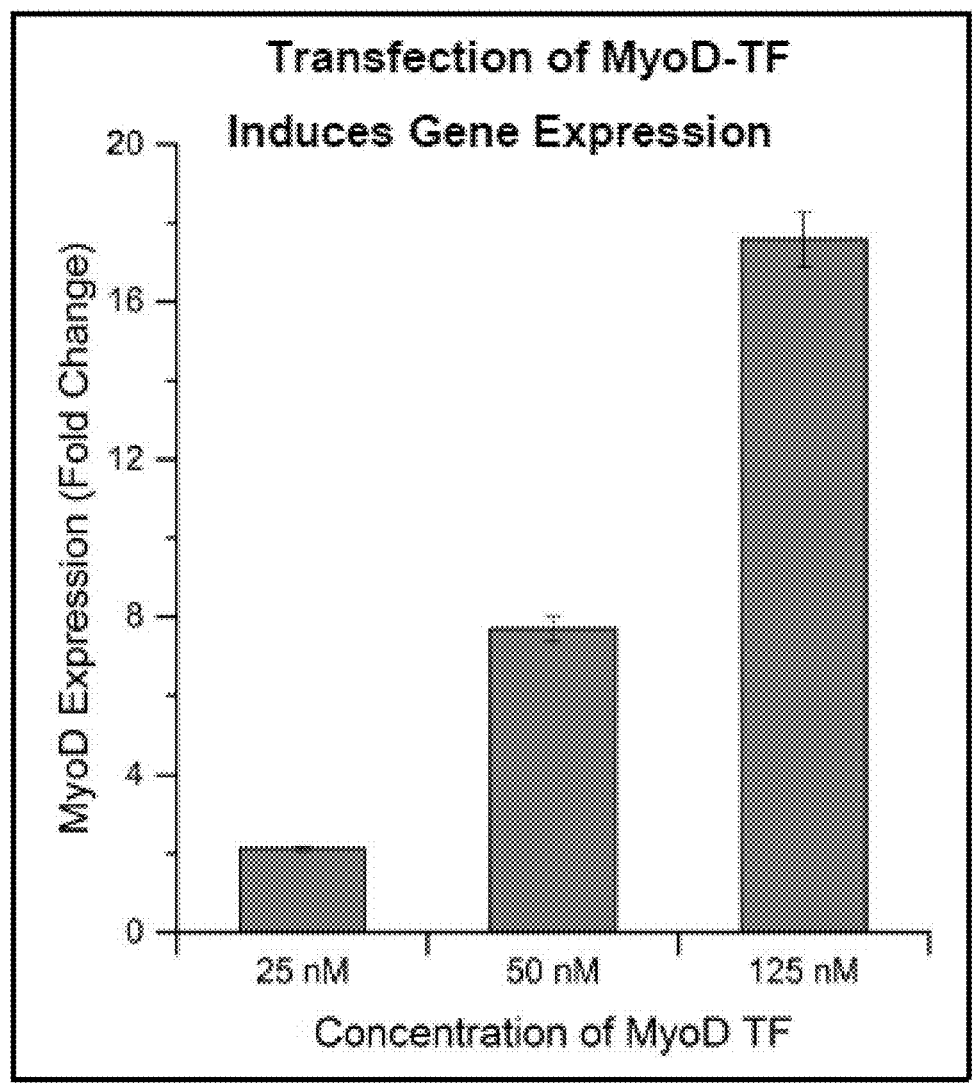

FIG. 11: Biologically Active Synthetic Nanoparticle Construct Activates Myogenic Genes. (a) After 7 days post-treatment with biologically active synthetic nanoparticle constructs with MRF domains, qPCR analysis reveals activation of targeted MRFs as well as significant expression of late-stage myogenic gene MYH1. (b) Distinct genes that represent the multipotency properties of ADMSCs were tested using qPCR analysis. Four genes, CD49d, CD44, CD90, and CD105, which are unique to ADMSC, were downregulated as compared to untreated control cells, thus confirming the stemness properties of the ADMSCs is greatly reduced upon treatment. Fold change is relative to untreated controls and Standard error and mean for all experiments was derived from three individual trials. (c) To confirm functionality, experimental controls were tested and evaluated. Specifically, nanoparticle constructs lacking individual domains, such as the AD and DBD, were testing on ADMSC and the gene expression was quantified by qPCR. The same myogenic genes in a were tested and showed negligible activation. (d) The MyoD-TF protein was commercially purchased and various concentrations were transfected into ADMSCs using a commercially available protein transfection kit. After 7 days, a concentration-dependent overexpression of the MyoD gene was observed. The concentration of MyoD-TF had to be significantly increased to achieve comparable gene expression.

DETAILED DESCRIPTION OF THE INVENTION

1. Overview

Unless otherwise defined, all technical and scientific terms used herein have the same meaning as commonly understood by one of ordinary skill in the art to which this invention pertains. In the case of conflict, the present document, including definitions will be controlled. This invention concerns biologically active synthetic nanoparticle constructs and their methods of use. Generally, the biologically active synthetic nanoparticle constructs are comprised of a biologically inert substrate, a plurality of DNA binding domains (DBD), and nuclear localization signals (NLS), wherein the plurality of DBD and the plurality of NLS are attached to a surface of the biologically inert substrate. Optionally, the nanoparticle constructs may have a plurality of activation domains (AD) or repression domains (RD) attached to the surface of the biologically inert substrate. The nanoparticle constructs may be used, for example, to enable significant increases in gene expression in, for example but not limited to, a recombinant vector, as well as expression of endogenous genes in a target organism or tissue sample. Suitable target organisms include any and all organisms of the domain eukaryota. Similarly, the nanoparticle constructs may be used, for example, to enable transcriptional repression in, for example but not limited to, a recombinant vector, as well as repression of endogenous genes in a target organism or tissue sample. By regulating and/or modifying transcriptional activity, the nanoparticle constructs may be used, for example, to activate or repress stem cell differentiation in a host organism or tissue sample. Furthermore, the nanoparticle constructs may be combined with a delivery vehicle for effective delivery into a host system.

2. Biologically Active Synthetic Nanoparticle Construct

The present invention provides biologically active synthetic nanoparticle constructs functionalized with both DBD and NLS components and optionally other components. The biologically active synthetic nanoparticle constructs are capable of initiating and repressing transcriptional activity, and therefore capable of regulating gene expression in living cells in a non-viral manner. These biologically active synthetic nanoparticle constructs have a small size and multi-functional properties to accommodate different types of biomolecules on a single nanoparticle, can permeate the plasma membrane, have enhanced localization within the nucleus while remaining intact, can initiate strong transcriptional activity of a reporter plasmid in a dose-dependent manner in live HeLa cell cultures, and are nontoxic to cells under the condition studied. The biologically active synthetic nanoparticle constructs can bind to select sequences on native DNA in HeLa cells and initiate transcriptional activity to overexpress endogenous genes. The versatile and tunable properties of biologically active synthetic nanoparticle construct establish this as an effective platform for applications that require endogenous gene regulation such as cellular reprogramming or stem cell differentiation.

The biologically inert substrate provides the base platform upon which the other elements of the biologically active synthetic nanoparticle construct are bound to. There are many types of biologically inert substrates that are appropriate for the present invention. For example, gold nanoparticles (AuNPs) are particularly effective as AuNPs are easy to synthesize, easy to handle, are FDA approved, and have multifunctional surfaces. However, there are many other substrates that are embodied by this invention. Other types of nanoparticles, for example but not limited to, magnetic nanoparticles, magnetic-core shell nanoparticles, silica nanoparticles, mesoporous nanoparticles, quantum dots, supramolecular nanoparticles, and polymer-based nanoparticles may all comprise the biologically inert substrate in the present invention.

DNA binding domains (DBD) are those moieties which are capable of binding directly to target nucleotide sequences of interest, for example but not limited to, a specific DNA sequence in a promoter region. This invention utilizes DBD for purposes of binding to nucleotide targets of interest to modulate transcription, for example, either activating or repressing transcription, and thus affecting certain biological processes, such as stem cell differentiation. The DNA binding domain is preferably comprised of a hairpin polyamide sequence motif comprised of N-methylpyrrole (Py) and N-methylimidazole (Im), as hairpin polyamide sequences exhibit high tunability and binding specificity as well as small molecular size. Hairpin polyamides function by binding to the minor groove of DNA through hydrogen bond interactions with a binding affinity comparable to naturally occurring DNA-binding proteins, as the Py and Im amino acids complement the A-T and G-C motifs on the DNA respectively. However, other DNA binding domains are embodied by the present invention, and may include, for example but not limited to, zinc finger domains, triple forming oligonucleotides, transcription activator-like effectors, oligonucleotide analogs, locked-nucleic acids, and peptide nucleic acids.

Nuclear localization signals (NLS) are amino acid sequences that allow for passage or import of a substance, typically an endogenous protein, into the cell nucleus by nuclear transport. This invention utilizes NLS to allow for effective nuclear transport of the biologically active synthetic nanoparticle construct into the nucleus so as to modulate transcriptional activity, as in eukaryotes, transcription occurs endogenously in the nucleus. Classic NLS are typically classified as monpartite or bipartite. Non classical NLSs include those derived from the M9 domain of hnRNP A1 and the KIPIK (SEQ ID NO: 35) sequence in yeast transcription repressor Matα2, and like classic NLS, are embodied by the present invention. Preferred NLS domains include those derived from SV-40 antigens, for example, domains bearing the sequence PKKKRKV (SEQ ID NO: 36). Others include those derived from HIV-1. One of ordinary skill in the art will recognize that any monopartite NLS following the Chelsky sequence K-K/R-X-K/R (SEQ ID NO: 37) is embodied by the present invention. Other NLS domains are embodied by the present invention, and include, for example but not limited to, bipartite NLSs such as those derived from nucleoplasmin, and other NLSs such as those listed in the table below:

| Name | Sequence |
| --- | --- |
| TAT (SEQ ID NO: 1) | GRKKRRQRRRPPQ |
| Penetratin (SEQ ID NO: 2) | RQIKIWFQNRRMKWKK |
| MAP (SEQ ID NO: 3) | KLALKLALKALKAALKLA |
| Transportin/TP10 (SEQ ID NO: 4)/ (SEQ ID NO: 5) | GWTLNS/ AGYLLGKINLKALAALAKKIL |
| VP22 (SEQ ID NO: 6) | NAKTRRHERRRKLAIER |
| MPG (SEQ ID NO: 7) | GALFLGFLGAAGSTMGA |
| Pep1 (SEQ ID NO: 8) | KETWWETWWTEWSQPKKKRKV |
| pVEC (SEQ ID NO: 9) | LLIILRRRIRKQAHAHSK |
| YTA2 (SEQ ID NO: 10) | YTAIAWVKAFIRKLRK |
| YTA4 (SEQ ID NO: 11) | IAWVKAFIRKLRKGPLG |
| M918 (SEQ ID NO: 12) | MVTVLFRRLRIRRACGPPRVRV |
| CADY (SEQ ID NO: 13) | GLWRALWRLLRSLWRLLWRA |

Activation domains (AD) are those domains that are capable of activating transcriptional activity, for example, by recruiting proteins such as RNAP and other factors that are required for transcriptional activation. ADs may be involved in triggering signaling cascades leading to expression of desired genes. In the present invention, ADs are preferably, but not necessarily, peptide sequences, and the peptide sequences are preferably, but not necessarily, synthesized in the D-isomer in order to resist intracellular degradation. One explicitly non-limiting example of an AD peptide domain is SGLMDLDFDDLADSGLMDLDFDDLADSGC (SEQ ID NO: 14). Other ADs are embodied by the present invention and may include, for example but not limited to, peptoids, amphipathic isoxasolidine, wrenchnolol, and amphipathic helix peptides.

Repression domains (RD) are those domains that are capable of repressing transcriptional activity, for example, by activating repressor proteins. In the present invention, RDs are preferably, not but not necessarily, peptide sequences, and the peptide sequences are preferably, but not necessarily, synthesized in the D-isomer in order to resist intracellular degradation. A list of RDs that embodied by the present invention include but are not limited to those found in the table below:

| Repression Domains | |
| --- | --- |
| WRPW | (SEQ ID NO: 15) |
| RLITLADHICQIITQDFAR | (SEQ ID NO: 16) |
| QINDLYSTDRPESAEAPDLQSWELR | (SEQ ID NO: 17) |
| ELQKSIGHKPEPTEEWELIKTVTEAHV | (SEQ ID NO: 18) |
| STPSSKTKDLGHNDKKSS | (SEQ ID NO: 19) |

The biologically active synthetic nanoparticle constructs may comprise further domains beyond the DBD, NLS, and any AD or RD. These additional domains may be biologically active or inert; they may, for example but not limited to, increase nuclear permeability, facilitate stability of the nanoparticle construct, increase the safety of the nanoparticle construct, decrease toxicity, or they may interact with various cellular components. These additional domains may participate in transcriptional activation or repression in a manner consistent with or independent of any AD or RD. They may synergistically increase the efficiency or potency of the biologically active synthetic nanoparticle construct. These examples are not meant to be limiting but merely demonstrative of the possibilities of additional domains.

The various domains of the biologically active synthetic nanoparticle construct, including the DBD, NLS, any AD, RD, or any other domains, are bound to a surface of the biologically inert substrate. Preferably, the domains are bound covalently via a crosslinker, for example a crosslinker having a formula SH—R—COOH. The R group may be for example but not limited to, any derivative of an alkyl or alkoxy chain, straight chain, branched, or otherwise, so long as the chain is not too short, for example the backbone having less than 3 carbons in length, or too long, for example the backbone having greater than 200 carbons. For example, the R group may be comprised of polyethylene glycol (PEG) or undecanoic acid. However one of ordinary skill in the art will recognize that there are many crosslinkers that are suitable for the purposes of this invention. Too short a chain risks aggregation, and too long a chain risks the overall size of the biologically active synthetic nanoparticle construct being unable to enter the nucleus due to size restrictions, thus rendering the construct ineffective. Preferably, the domain amino groups are coupled to crosslinker carboxylic acids via conventional EDC/NHS coupling, however one of ordinary skill in the art will recognize that there are many other chemical routes to conjugate the molecules, for example but not limited to, active ester coupling utilizing carbodiimides such as those reactions utilizing dicyclohexylcarbodiimide (DCC) and diisoproylcarbodiimide (DIC) or coupling reactions utilizing triazoles such as 1-hydroxy-benzotriazole (HOBt) and 1-hydroxy-7-aza-benzotriazole (HOAt).

3. Methods of Use of Biologically Active Synthetic Nanoparticle Constructs

A. Transcriptional Activation

One aspect of the present invention is the use of biologically active synthetic nanoparticle constructs in order to activate transcription of particular target genes or other DNA sequences. Endogenous genes are transcribed when transcriptional basal machinery, comprised of compounds including but not limited to compounds such as general transcription factors (TFs), RNAP, SAGA, and mediators, are directed to a particular target gene sequence and thus initiate transcription. The biologically active synthetic nanoparticle constructs as described in this invention are capable of activating transcription. For methods of transcriptional activation, the biologically active synthetic nanoparticle constructs are comprised of a biologically inert substrate, DBD, NLS, and AD. When in this composition, the biologically active synthetic nanoparticle constructs mimic natural transcription factors, which are comprised of a DBD and AD. It is the presence of AD that distinguishes the biologically inactive synthetic nanoparticle constructs used for transcriptional activation from those used in transcriptional repression, as the ADs are involved in recruitment of the endogenous transcriptional basal machinery such as RNAP and mediators, thus initiating transcription. The NLS allows the biologically synthetic nanoparticle constructs to enter the nucleus, which is essential because transcription takes place in the nucleus. The DBD binds to enhancer regions of DNA, allowing the AD to recruit the components needed for transcriptional activation.

B. Transcriptional Repression

Another aspect of the present invention is the use of biologically active synthetic nanoparticle constructs in order to repress transcription of particular target genes or other DNA sequences. In addition to activating transcription, the biologically active synthetic nanoparticle constructs as described in this invention are capable of repressing transcription. For methods of transcriptional repression, the biologically active synthetic nanoparticle constructs are comprised of a biologically inert substrate, DBD, NLS and optionally RD. The optional presence of an RD may enhance the efficacy of transcriptional repression by activating repressor proteins, which then in turn bind to silencer regions. As with transcriptional activation, the NLS allows the biologically synthetic nanoparticle constructs to enter the nucleus, which is essential because transcription takes place in the nucleus. However, unlike transcriptional activation, the DBD has a different role in methods of transcriptional repression. The DBD may bind at or near the promoter region and physically block RNAP from initiating transcription via steric hindrance. This is opposed to the DBD binding at an enhancer region and recruiting transcriptional machinery proteins.

C. Modulation of Stem Cell Differentiation

Another aspect of the present invention is the use of biologically active synthetic nanoparticle constructs in order to modulate stem cell differentiation. Because the biologically active synthetic nanoparticle constructs of this invention may either activate or repress transcription in a nonviral manner, the nanoparticle constructs of this invention may be useful for stem cell differentiation applications. In preferred embodiments, the stem cells undergoing differentiation are adipose-derived mesenchymal stem cells (ADSCs). ADSC, including adipose-derived mesenchymal stem cells (ADMSCs), are multipotent stem cells that have been shown to differentiate into osteogenic, chondrogenic, adipogenic, myogenic, or neurogenic lineages.

D. Vehicle Delivery Platform

Yet another aspect of the present invention is the use of a cell differentiation medical device that incorporates biologically active synthetic nanoparticle constructs. These biologically active synthetic nanoparticle constructs can be comprised of any combination of biologically inert substrate, DBD, NLS and optional AD or RD domains as disclosed in this invention. In this aspect of the invention, a transcription pre-initiation complex (TPC) ligand is attached to the surface of the biologically inert substrate, the TPC being designed to direct the biologically active synthetic nanoparticle construct to a specific area of an organism. The TPC is comprised of various proteins including RNAP, mediators, and other proteins and/or enzymes that work synergistically to initiate transcriptional activity. The optional AD may function to recruit the TPC to binding sites on targeted genes and may initiate transcriptional activity of those targeted genes.

A transport vehicle for implementation of the biologically active synthetic nanoparticle constructs may come in a variety of forms based upon the particular tissue which is effected by the cell differentiation medical device. The inclusion of the TPC in the biologically active synthetic nanoparticle construct ensures that the cell differentiation medical device is directed to where is needed within the organism.

The transport vehicle may optionally include components for regeneration of tissues. ADSCs may be included with the cell differentiation medical device in the transport vehicle.

For internal tissue use, the transport vehicle may optionally comprise an intravenous drip further including a saline solution and the cell differentiation medical device. The transport vehicle will recognize the importance of the size of a intravenous needle used and any container used in order to ensure free flow of the intravenous drip into the body.

For topical use, the transport vehicle may optionally include a biodegradable polymer scaffold.

The transport vehicle may further comprise biodegradable hydrogel for direct topical application of the cell differentiation medical device to a specific area of a surface of an organism. A hydrogel may significantly enhance the use of a growth media for cellular growth upon stimulation by the biologically active synthetic nanoparticle constructs of the cell differentiation medical device.

E. Tissue Regeneration

Further aspects of the present invention include methods to regenerate tissue. The method comprises preparing any cell differentiation medical device as disclosed in this invention and delivering the cell differentiation medical device to an organism by means that ensure the cell differentiation medical device is directed to an area or areas where tissue regeneration is desired. This embodiment may further comprise combining a cell type (somatic cell or stem cell) that can be induced to generate functional cells for the tissue regeneration and transplantation, saline solution, and the cell differentiation medical device in an intravenous solution and delivering the intravenous solution to tissue. This embodiment may also further comprise preparing any cell differentiation medical device as disclosed in this invention and attaching the device topically to an organism.

4. Examples

A. Synthesis of Biologically Active Synthetic Nanoparticle Constructs

Example A1

Synthesis of Gold Nanoparticles: While many biologically inert substrates can be utilized in the present invention, gold nanoparticles were chosen having an approximate diameter of 9 nm were prepared by the Ferns method of citrate reduction of $HAuCl_4$ following establish protocols. All glassware was cleaned in aqua regia (ratio of 3 HCl:1 $HNO_3$, handled with extreme caution), then rinsed with nanopore water and oven dried. A 50 mL aqueous solution of 1 mM $HAuCl_4$ was heated to a reflex while stirring. Then 8 mL of 1% (by weight) sodium citrate was quickly added, resulting in a change in solution color from yellow to ruby red. After the color change, the solution was refluxed for another 5 minutes, then cooled to room temperature and filtered using a 0.45 μm syringe filter. Size distribution was characterized using transmission electron microscopy (TEM) and dynamic light scattering (DLS), and concentration was obtained using UV-vis spectroscopy.

Gold Nanoparticle Conjugation: 10 nm gold nanoparticles (AuNPs) were conjugated to ligands using a two step method. The first step involves ligand exchange on the AuNP with the linker molecule 11-mercaptoundecanoic acid (MUA). First, from a stock solution of MUA dissolved in ethanol, 1 mM MUA was added to the AuNP solution (pH=11, NaOH) and allowed to stir at room temperature for 24 hr. The solution was then filtered three times using a 10,000 MWCO filter (Millipore) and re-suspended in distilled water. The second step involves conjugated the ligands to the AuNP via the carboxylic acid of the MUA. To the AuNP solution, adjusted to pH=6.5 by adding 5 mM MES (Hampton Research), was added 0.3 mM of 1-ethyl-3-(3-dimethylaminopropyl) carbodiimide) (EDC) (Sigma) and 0.75 mM of N-hydroxysuccinimide (NHS) (Acros Organics) and allowed to stir for 2 hr at room temperature. The solution was filtered three times using a 10K MWCOF, and re-suspended in 1 mM MES water. Immediately afterwards, a solution containing 10 molar excess of NLs, AD, and DBD, in a molar ratio of 5:4:1 (NLS:AD:DBD), was added drop-wise to the AuNP solution, adjusted to pH=7.2 by adding 50 mM HEPES (Cellgro) prior to addition of biomolecules, and allowed to stir for 2 hr. The AuNP solution was filtered three times using a 10,000 MWCO to remove unreacted molecules.

Quantifying Peptide Ratio: The amount of peptides in the solution was calculated by performing HPLC (Agilent LC 1100) using a Zorbax Extend-C18 Solvent Saver Plus, 3.5 μm, 3.0×150 mm column. The peptide solution before conjugation and the supernatant solution after conjugation, which contained un-reacted peptides, were both analyzed using HPLC to calculate the exact number of moles of each peptide. The exact number of moles for each peptide was calculated using a standard curve comparing the concentration and area. The difference in moles for each peptide before and after conjugation was calculated. The ratio of the difference in moles is attributed to the ratio on the nanoparticle. The nanoparticles were centrifuged at 12,000 RPM for 20 minutes and the supernatant was collected.

Biologically Active Synthetic Nanoparticle Construct Characterization: The biologically active synthetic nanoparticle construct was characterized using multiple techniques. First, the concentration of the gold nanoparticles and confirmation of conjugation was found using UV-visible absorption spectra (Varian Cary 5000 UVVis-NIR Spectrophotometer). Second, Dynamic Light Scattering (Malvern Zetasizer Nano-ZS90) was utilized to measure the size and zeta potential (surface charge) of the AuNP construct after each conjugation step to find the hydrodynamic diameter and surface charge respectively. Third, the morphology of the AuNP core was determined using transmission electron microscopy (TEM) analysis. The AuNPs were drop-cast on the Holey-carbon grids (Electron Microscopy Sciences), allowed to dry overnight under vacuum, and subsequently imaged using a JEOL JEM-2010F high-resolution TEM operated at an accelerating voltage of 200 kV.

Peptide Synthesis: The peptides were purchased from commercial companies. The AD, having a sequence of CGSDALDDFDLDMLGSDALDDFDLDMLGS-NH$_2$ (SEQ ID NO: 20), was purchased from Invitrogen. The NLS, having a sequence of CGGGPKKKRKVED-OH (SEQ ID NO: 21), was purchased from GenScript. All peptides were stored and dissolved as per the manufacturer recommendations.

B. Synthesis, Nuclear Transport, and Transcriptional Activation

Example B1—HeLa Cells

Synthesis and Characterization of Construct: In this example, synthesis of the biologically active synthetic nanoparticle constructs was carried out by coating gold nanoparticles (AuNP) with mercaptoundeconic acid (MUA) and then conjugating the AuNP to AD, DBD, and NLS peptide components via EDC/NHS coupling (FIG. 3).

The DBD utilized was a polyamide structure comprised of methylpyrrole (Py) and N-Methylimidazole (Im) amino acids that complement the A-T and G-C motifs on the DNA respectively. Using a solid-phase synthesis method, the polyamide was synthesized with amino acids arranged in the order of ImPyPyPy-γ-PyPyPy-β-Dp-NH2 (where γ is γ-aminobutyric acid, β is β-alanine, and Dp is dimethylaminopropylamide), to recognize the 5'-WGWWWW-3' (W=A or T) (SEQ ID NO: 22) DNA sequence (FIG. 3c). This polyamide sequence was designed to complement a reporter gene in order to quantify gene expression magnitude. The AD was demonstrated to effectively recruit required proteins such as mediators, RNA polymerase II, and SAGA to the binding site and initiate transcriptional activity. This AD was synthesized in the D-form to resist degradation by intracellular proteases. The NLS peptide was derived from SV40 large T-antigen and functions to facilitate entry of the biologically active synthetic nanoparticle construct into the nucleus.

The size and surface charge was measured and yielded a final hydrodynamic diameter of the biologically active synthetic nanoparticle construct to be 34.0 nm, having a surface charge of −32.5 mV (FIG. 3b). This hydrodynamic diameter indicates that the AD has a linear conformation after conjugation, because the theoretical diameter (found using bond lengths and assuming liner conformation) of the biologically active synthetic nanoparticle construct is 35.2 nm.

Transmission electron microscopy (TEM) of the biologically active synthetic nanoparticle constructs confirmed that surface functionalization with AD and DBD components does not affect size distribution or monodispersity of the nanoparticles. The surface functionalization on the gold nanoparticles did lead to a shift of the surface plasmon band, indicating a change in the refractive index due to surface adsorption of STF components. The ratio of ligands on the nanoparticle surface, quantified by HPLC analysis, was found to be approximately 7:2:1 (NLS:AD:DBD). To calculate this ratio, HPLC analysis was performed to calculate the moles of each peptide in both the solution before conjugation and the supernatant solution after conjugation containing unreacted peptides. The mole ratio of the difference is the ratio of the different domains on the biologically active synthetic nanoparticle constructs and is shown in the table below.

| Mole Ratio of Domains on Biologically Active Synthetic Nanoparticle Construct Surface | |
|---|---|
| NLS | 68.2 ± 1.0% |
| AD | 22.8 ± 2.6% |
| DBD | 9.0 ± 2.1% |

The ratio of AD was increased relative to the DBD to mimic the potent endogenous transcription factor p53 while the NLS peptide ratio was increased to ensure sufficient nuclear uptake. Conjugating both the DBD and AD domains on the same nanoparticle mimics natural TFs which contain both domains on a single protein in close proximity of each other.

The biologically active synthetic nanoparticle constructs were evaluated for their ability to penetrate the plasma membrane and efficiently enter the nucleus. To monitor intracellular location, the AD on the biologically active synthetic nanoparticle constructs was tagged with a fluorescent dye then incubated in HeLa cell cultures for 4 hours. The culture media was replaced with fresh media, and 48 hours later the cells were fixed and imaged. As evidenced by the overlap of the biologically active synthetic nanoparticle constructs and cell nucleus, a moderate number of biologically active synthetic nanoparticle constructs were able to target and penetrate the nuclear envelope. Additionally, a cross-sectional side view image showed the biologically active synthetic nanoparticle constructs scattered throughout the nucleus in the vertical plane. This confirmed the biologically active synthetic nanoparticle construct was not merely resting on the upper surface of the nucleus. Furthermore, a 3-dimensional fluorescence motion image of a HeLa cell showing biologically active synthetic nanoparticle constructs scattered throughout the cytoplasm and nucleus provided further confirmation of the nuclear uptake. Based on these fluorescence images, it was concluded that the biologically active synthetic nanoparticle constructs are able to enter the nucleus with the DBD and AD components still attached.

Transmission electron microscopy (TEM) was used to image cellular cross-sectional to show AuNPs within nucleus. The TEM image showed the interface between the cytoplasm the nucleus, with the biologically active synthetic nanoparticle constructs located inside the nucleus. This result indicates that the NLS peptide is still attached to the AuNP because the nuclear membrane is highly selective in only allowing substances with certain markers, such as the NLS peptide, to penetrate. Furthermore, the tight packing of the molecules on the AuNP surface likely causes steric inhibition of protease degradation. Combining the results of the fluorescence and TEM images, it was concluded that the functional components on the biologically active synthetic nanoparticle constructs remain intact without being cleaved from the nanoparticle surface.

Cell Culture and AuNP Uptake: HeLa cells were cultured in Dulbecco's Modified Eagle medium with high glucose (DMEM) (Invitrogen) supplemented with 10% fetal bovine serum, 1% glutamax (Invitrogen) and 1% streptomycin-penicillin antibiotic in a 37° C. humidified incubator with 5% CO2. Prior to transfection, 25,000 HeLa cells were seeded in a well of 24 well-plate. After 24 hr, the cells were incubated with a mixture of the Biologically active synthetic nanoparticle construct solution, 0.5 μg of the reporter plasmid, and X-tremeGENE (Roche) in Opti-MEM medium (Invitrogen). After 4 hr, the cells were washed twice with PBS and fresh culture medium was added. After 48 hr, the alkaline phosphatase level in the culture medium was tested using the SEAP Chemiluminescence Kit 2.0 (Clontech) by following the manufacturer protocol. An MTS assay (Promega) was also performed at this time to test cell viability.

Cell Transmission Electron Microscopy (TEM): HeLa cells were cultured with biologically active synthetic nanoparticle constructs using the same method as above, but in a 6 cm cell culture dish. 48 hr post-transfection, the cells were trypsinized and fixed with Trump's Fixative (Electron Microscopy Sciences) for 1 hr, washed with sodium cacodylate buffer (Electron Microscopy Sciences), suspended in a 1% osmium tetroxide solution for 1 hr, washed with water, and then progressively dehydrated with ethanol (50, 70, 80, 95, 100%). Then the cells were embedded in epoxy resin using the Low Viscosity Embedding Media Spurr's Kit (Electron Microscopy Sciences) following the manufacturer's protocol. The images were obtained with the JEOL 100CX TEM.

Quantification of Endogenous Genes Using qPCR: It was also determined that endogenous genes on the HeLa cell DNA genome can be activated and overexpressed. Several endogenous genes were identified with complementary sequences on the promoter region as the DBD. The following table shows the number of binding sites that the DBD can bind on the promoter sequence of the four overexpressed endogenous genes. Binding sites are within 1000 bp 5' from the transcription start site.

| Gene | Number of Binding Sites on Promoter Region |
|---|---|
| LGALS8 | 36 |
| CDC26 | 23 |
| ACTL8 | 21 |
| NS3TP1 | 41 |

Total RNA was extracted with TRIzol reagent (Invitrogen) and was reverse transcribed to cDNA with Superscript III Reverse Transcriptase (Invitrogen). Conventional quantitative RT-PCR was performed using a SYBR Green PCR Master Mix (Applied Biosystems) on a StepOnePlus Real-time PCR System (Applied Biosystems). Primers sequences and the expected band size were as follows:

| Target | Forward Primer | Reverse Primer | Expected Size (bp) |
|---|---|---|---|
| LGALS8 | 5'CCTATGACACGCCTTTCAAAAGA-3' (SEQ ID NO: 23) | 5'CAGCACCATAATCACGATCTCAA-3' (SEQ ID NO: 24) | 56 |
| CDC26 | 5'ATTCGAAAGGACCTGGAGACCC-3' (SEQ ID NO: 25) | 5'-ATCACTGCTAAGCCCAATGGC-3' (SEQ ID NO: 26) | 96 |
| ACTL8 | 5'-CTGCGGACCGAAAGAAGATG-3' (SEQ ID NO: 27) | 5'-ATGCAGCAACTCAAACAGGAT-3' (SEQ ID NO: 28) | 47 |
| NS3TP1 | 5'-ATTCTCGTCATCGTGTCCGC-3' (SEQ ID NO: 29) | 5'CATCCAGGAAAGGAAATCTTGCT-3' (SEQ ID NO: 30) | 156 |

Results: HeLa cells were exposed to the biologically active synthetic nanoparticle constructs for 4 hours, then culture media was replaced with fresh media, and after 48 hours the cells were lysed and RNA was extracted. Quantification of endogenous gene activation was performed using qPCR and showed that activity of LGALS8 and CDC26 was overexpressed 65% and 20% respectively, relative to cells treated with unmodified AuNPs. This further confirms that the biologically active synthetic nanoparticle constructs are stable and small enough to navigate within the chromosomal DNA, seek complementary gene motifs, and initiate transcriptional activity to activate targeted genes. Overexpression of endogenous genes high-lights the versatility and functionality of the biologically active synthetic nanoparticle constructs, thus proving that these nanoparticle constructs can behave and function like natural TFs.

It was confirmed that the biologically active synthetic nanoparticle constructs can mimic the function of endogenous TFs, which includes initiating transcription and overexpressing desired genes. A reporter plasmid was designed containing a response element of six copies of the 5'-TGT-TAT-3' sequence (SEQ ID NO: 31), which is complementary to the DBD (FIG. 4a; 5'-GCGGTACCGCTAGCAGCT-TATAACATTCCATATGTTATACATAACATTCCATAT-GTTATACATAACATTCCATATGTTATACGTCGA-CAAGCTATGAGATCTAGACTCTAGAGGGTATATAA TGGAAGCTCGACTCCAGCTTGGCATTCCGGTACT-GTTGGTAAAAGCTTCGAATA-3') (SEQ ID NO: 32). This response element was inserted in the pSEAP2-Basic Vector (Clontech), between KpnI (GGTACC) (SEQ ID NO: 38) and HindIII (AAGCTT) (SEQ ID NO: 39) sites. Transcription of this sequence on the reporter plasmid leads to the production of alkaline phosphatase, which is secreted into the cell culture media and measured. Because this secreted alkaline phosphatase (SEAP) is directly proportional to the magnitude of induced transcriptional activity, the functionality and potency of the biologically active synthetic nanoparticle constructs can be evaluated. Co-transient transfection of the biologically active synthetic nanoparticle constructs and the reporter gene was carried out for 4 hr and the culture media was evaluated for SEAP after 48 hours (FIG. 4b). Analysis of SEAP shows that the biologically active synthetic nanoparticle constructs can initiate transcription and overexpress the reporter plasmid by over a 15 fold increase in comparison to unmodified AuNPs (FIG. 4c), while maintaining high cell viability. Furthermore, the contribution of each component on the biologically active synthetic nanoparticle constructs for initiating transcriptional activity was tested by selectively removing one component at a time. Subsequent SEAP analysis of these altered biologically active synthetic nanoparticle constructs showed limited gene expression, thus confirming the importance of each component (FIG. 4c).

Moreover, when HeLa cells were exposed to varying concentrations of the biologically active synthetic nanoparticle constructs, there was a dose-dependent expression of the SEAP (FIG. 4d), indicating that the extent of gene expression can be exogenously modulated. These results are consistent and surpass previous reports of using a polyamide based STF for gene activation. Based on these results, it has been demonstrated that all three components on the present biologically active synthetic nanoparticle constructs work synergistically to induce profound gene expression in a dose-dependent manner.

C. Further Transcriptional Activation

Biologically active synthetic nanoparticle constructs are an effective platform to mimic the gene regulating properties of transcription factors. To demonstrate the robust and tunable properties of biologically active synthetic nanoparticle constructs to overexpress genes specific for differentiation, several polyamide DBDs specific for differentiation genes including Oct4, and Sox9 were synthesized. Overexpression of these differentiation genes was demonstrated.

Example C1—Oct4 Activation

The transcription factor Oct4 is responsible for activation of the Oct4 gene, which when overexpressed, induces the reprogramming of somatic cells (e.g. fibroblasts) into pluripotent stem cells. Biologically active synthetic nanoparticle constructs were synthesized in a manner as previously disclosed including a DBD specific for Oct4. The DBD specific for Oct4 (Oct4-DBD) is depicted in FIG. 5. Upon administration of biologically active synthetic nanoparticle construct bound to Activation of the Oct4 gene was observed in FIG. 5.

Example C2—Sox9 Activation and Chrondrogeneic Differentiation

The gene Sox9 is involved in neural development, specifically that repression of Sox9 leads to neural development. Activation of the Sox9 gene results in stem cell differentiation into chondrocytes. Furthermore, the p300 pathway enhances expression of the Sox9 gene. A small molecule called CTB [N-(4-chloro-3-trifluoromethyl)-2-ethoxy-6-pentadecylbenzamide] regulates histone modification via the p300 pathway. Adding CTB to the synthetic nanoparticle constructs makes the constructs more closely mimic TF proteins, because TF proteins have a domain for histone modification. Biologically active synthetic nanoparticle constructs were synthesized in a manner as previously disclosed including a DBD specific for Sox9. The biologically active synthetic nanoparticle complexes of the immediate example further comprised CTB domains that were attached to the surface of the biologically inert substrate. By supplementing the biologically active synthetic nanoparticle complexes with CTB, increased histone acetyltransferase activity was recorded (FIG. 6) over those nanoparticle complexes without CTB. This resulted in enhanced expression of Sox9 for chondrogenic differentiation, evidenced by increased expression of Aggrecan, a distinct chondrogenic marker, 7 days post transfection by the biologically active synthetic nanoparticle constructs (FIG. 6).

D. Transcriptional Repression

Example D1—GFP Repression

Biologically active synthetic nanoparticle constructs were initially synthesized in a manner as disclosed in Example E1 below, except that the DBD was specific for GFP, as depicted in Figure X, and there was use of an RD (WRPW) instead of an AD. The results showed that this particular biologically active synthetic nanoparticle construct was capable of repressing GFP. When the biologically active synthetic nanoparticle constructs were transfected into GFP-labeled rat neural stem cells (rNSCs), an obvious trend of decreased GFP signal was observed. After 48 hours, the GFP was repressed by almost 34%. After 4 days, the GFP signal was reduced by almost 48%. The most effective biologically active synthetic nanoparticle constructs had both the RD and DBD for GFP, although constructs that lacked RD were still effective in repressing transcription (FIG. 7).

Example D2—Sox9 Repression

The gene Sox9 is involved in neural development, specifically that repression of Sox9 leads to neural development. In human neural progenitor cells (hNPCs), if the Sox9 gene is repressed, generation of neurons occurs at an enhanced rate. Biologically active synthetic nanoparticle constructs are initially synthesized in a manner as disclosed in Example E1 below, except that the DBD is specific for Sox9, and an RD (WRPW) is used instead of an AD. The hairpain polyamide DBD binds to the Sox9 promoter and sterically blocks RNAP, thus repressing transcription. Furthermore, the RD acts as a corepressor and inhibits the recruitment of transcriptional basal machinery. Thus, transcription of Sox9 is repressed, and neural differentiation is able to occur (FIG. 8).

E. Modulation of Stem Cell Differentiation

Example E1—Myogenic Regulatory Factors

The process of generating muscle cells, known as myogenesis, is governed by a group of four TFs called myogenic regulatory factors (MRFs), which include MyoD, Myogenin, Myf5, and Mrf4, and have been demonstrated to play a critical role in generating muscle cells from both somatic and stem cells.

Synthesis of Biologically Active Synthetic Nanoparticle Construct: The biologically active synthetic nanoparticle construct utilized in this example was comprised of i) a gold nanoparticle (AuNP) that acts as the linker domain to tether the DBD, AD, and NLS ii) polyethylene glycol (PEG)-based molecules that prevent intracellular degradation and increase the stability of the biologically active synthetic nanoparticle construct in physiological conditions, iii) a hairpin polyamide DBD, iv) an AD, and v) an NLS (FIG. 9). The DBD was a hairpin polyamide DBD specific for MRFs (termed MRFDBD) with the sequence PyPyPy-β-PyPyIm-γ-PyPyPy-β-PyImPy-β-Dp to complement a consensus sequence 5'-CANNTG-3' (N=any base pair) (SEQ ID NO: 33). MRFs activate muscle-specific transcription by binding to the previous consensus sequence. The DBD was synthesized using an established solid phase synthesis procedure. After synthesis, surface plasmon resonance was used to confirm that MRFDBD had a strong nanomolar binding affinity of 9×10-9 M to the target sequence. The AD utilized was SGLMDLDFDDLADSGLMDLDFDDLADSGC (SEQ ID NO: 14) and was in the D-isomer. The NLS was CALNNAGRKKRRQRRR (SEQ ID NO: 34). The DBD, AD, and NLS were attached to the surface of the AuNP via a PEG crosslinker and attached by EDC/NHS coupling.

First the amine terminated AD, NLS, and DBD molecules were conjugated to linker molecules, SH-PEG-COOH (Thiol-PEG-Carboxy 1 KDa [Creative PEGWorks, PBL-8073]). The PEG molecule was dissolved into a 50 mM solution in ethanol. Then, 50 mM of 1-ethyl-3-(3-dimethylaminopropyl) carbodiimide) (EDC) (Sigma) and 50 mM of N-hydroxysuccinimide (NHS) (Acros Organics) was added to this solution and then placed on a shaker for 1 hour to activate the carboxyl group. Afterwards, a 5 mM solution of the STF molecule was added to the solution and allowed to react at room temperature for 2 hr. The three STF molecules with PEG (PEG-MRF-DBD, PEG-TAP, and PEG-CPP), they were coated on the synthesized 10 nm AuNPs. A solution containing 10 molar excess of PEG-MRF-DBD, PEG-TAP, and PEG-CPP with a mole ratio of 2:2:1 respectively was added drop-wise to the AuNP solution and allowed to stir for 2 hours. The biologically active synthetic nanoparticle constructs were now functional, and were filtered three times using a 10,000 MCWO filter (Millipore) to remove unreacted molecule and adjust the volume to concentration the solution. The dyelabeled biologically active synthetic nanoparticle constructs, used for tracking intracellular localization, was constructed by conjugating Alexa Flour 594 (Invitrogen) fluorescent dye to the AD (the transactivation peptide). Specifically, the free carboxy group on PEG-TAP was further conjugated to the Alexa Flour 594 Hydrazide dye via EDC/NHS coupling as described above.

ADSMC Culture and Myogenic Differentiation: The human adipose-derived mesenchymal stem cells (ADMSCs) (American CryoStem) and the 0.5% FBS growth media was purchased and the cell were expanded using the manufacture's protocol. The ADMSCs were grown on fibronectin (2 µg/cm2, Millipore) coated culture dishes, and maintained at 37° C. in a humidified incubator with 5% $CO_2$. For consistency, all experiments were carried out on cells between passages 2 to 4. For myogenic differentiation experiments, ADMSCs were seeded in a 24-well plate at a density of 20,000 cells per well. After 24 hr, a 1 nM of the biologically active synthetic nanoparticle constructs was incubated with the cells for 4 hours, after which, the cells were washed twice with PBS and fresh media was added. On Day 1, the media was replaced with myogenic growth media, which consists of 2% horse serum (Sigma), human transferrin (2.5 µg/mL, Sigma), human insulin (5 µg/mL, Life Technologies), and 1% penicillin and streptomycin (Life Technologies) in high glucose DMEM (Dulbecco's Modified Eagle Medium, Invitrogen). A 1 nM of was the biologically active synthetic nanoparticle constructs was transfected on day 2 for 4 hours and washed twice with PBS and then fresh myogenic media was added. The cells were allowed to differentiate for 7 days in myogenic growth media, which was replaced with fresh media every other day. The MyoD-TF (Abcam, #ab134857) was transfected into ADMSCs on Day 0 and Day 2 using a commercially available kit (Thermo Scientific, Pro-Ject Protein Transfection Reagent #89850) and following the manufacturer's protocol.

Immunocytochemistry: To investigate the nuclear localization of the dye-labeled biologically active synthetic nanoparticle constructs in ADMSC cells, the media was removed and the cells were fixed for 15 minutes in formalin (Sigma) followed by two washes with PBS. The nucleus was stained with DAPI (Life Technologies) for 30 minutes and then washed with PBS three times. To investigate the extent of myogenic differentiation, on Day 7, the media was removed and fixed with formalin for 15 minutes and then washed twice with PBS. Cells were then permeabilized with 0.1% Triton X-100 in PBS for 10 minutes and non-specific binding was blocked with 5% normal goat serum (NGS, Life Technologies) in PBS for 1 hour at room temperature. To study the extent of myogenic differentiation, the primary mouse antibody against Myosin (1:200 dilution, Sigma) and the primary rabbit antibody against Myogenin (1:200 dilution, Santa Cruz Biotechnology) was used. Following the manufacturer's protocol, the fixed samples were incubated overnight at 4° C. in a solution of these antibodies in PBS containing 10% NGS. After washing three times with PBS, the samples were incubated for 1 hr at room temperature in a solution of anti-mouse secondary antibody labeled with Alexa Flour 647 (1:100, Life Technologies), anti-rabbit secondary antibody labeled with Alexa Flour 546 (1:100, Life Technologies), and DAPI (1:100, Life Technologies), in PBS containing 10% NGS. After washing thrice, all the samples were imaged using the Nikon T2500 inverted fluorescence micro scope.

Results: ADMSCs were treated with the biologically active synthetic nanoparticle constructs and then a myogenic media was introduced on day 1 to support muscle growth. After 7 days, expression of muscle-specific markers and phenotype changes were analyzed. As evidenced by expression of myogenin, a ubiquitous myogenic marker, and myosin, a distinct muscle marker, we observed generation of myocytes, which are elongated, tubular muscle fiber cells, from ADMSC using the biologically active synthetic nanoparticle constructs (FIG. 10c). Furthermore, the induced myocytes displayed mature muscle fiber characteristics as evidenced by the distribution of multiple nuclei and the formation of striations in the aligned muscle fiber. These striations are actin and myosin filaments called myofibrils, and upon further inspection, the development of myofibrils were verified through the fluorescence intensity profile showing six distinct peaks that represent individual myofibril filament (FIG. 10d).

This myogenic differentiation was further confirmed using qPCR to quantify the activation of muscle-specific genes. Two distinctive intermediate myogenic genes, desmin and enolase, along with all four MRFs were effectively activated in cells treated the biologically active synthetic nanoparticle constructs (FIG. 11a). Furthermore, the late-stage myocyte marker, myosin heavy chain (MYH1), was up-regulated by almost 28 fold (FIG. 11a). This evidence strongly suggests that the gene expression potency induced by the biologically active synthetic nanoparticle constructs is sufficient to trigger downstream myogenic genes involved in generating and supporting myocyte growth. As a result of activating myogenic genes, genes distinct for ADMSC's were suppressed and significantly down-regulated (FIG. 11b), thus indicating successful genetic reprogramming. Furthermore, the contribution of each domain on the biologically active synthetic nanoparticle constructs was evaluated through experimental controls, which included modified biologically active synthetic nanoparticle constructs lacking an AD or DBD (FIG. 11c). Because these controls are unable to activate myogenic genes beyond basal levels, it signifies the synergistic function and contribution of each domain in initiating transcription. Moreover, cell viability assays indicated the viability of generated myocytes to be 97.6±1.1%, as compared to the untreated control. Collectively, these findings establish that genetic reprogramming by the biologically active synthetic nanoparticle constructs can initiate transcriptional activity of differentiation-specific genes to generate mature muscle fibers from stem cells.

The effectiveness of the biologically active synthetic nanoparticle constructs were compared against commercially available synthetic transcription factor proteins, such as MyoD-TF. Various concentrations of MyoD-TF were transfected into ADMSCs using a commercially available protein delivery kit. After 7 days, gene expression levels of MyoD were upregulated (FIG. 11d), however, the gene expression levels we less than those induced by the biologically active synthetic nanoparticle constructs. A 1 nM concentration of the biologically active synthetic nanoparticle constructs overexpressed MyoD by almost 12-fold, and comparatively, the concentration of the MyoD-TF had to be significantly increased to generate a comparable result (FIG. 11d). This result suggests that the function and potency of the biologically active synthetic nanoparticle constructs is comparable, or perhaps even outperforms, conventional methods of TF protein delivery.

CONCLUSION

It will be appreciated by those skilled in the art that changes could be made to the embodiments described above without departing from the broad inventive concept thereof. It is understood, therefore, that this invention is not limited to the particular embodiments or examples disclosed, but it is intended to cover modification that are within the spirit and scope of the present invention as defined by the appended claims.

What is claimed is:

1. A biologically active synthetic nanoparticle construct comprising:
   i. a biologically inert substrate;
   ii. a plurality of single copies of DNA binding domains;
   iii. a plurality of single copies of nuclear localization signals; and
   iv. a plurality of single copies of transcriptional activation domains,
   wherein the plurality of DNA binding domains are each individually covalently attached to a surface of the biologically inert substrate,
   wherein the plurality of nuclear localization signals are each individually covalently attached to the surface of the biologically inert substrate,
   wherein the plurality of transcriptional activation domains are each individually covalently attached to the surface of the biologically inert substrate,
   wherein the plurality of transcriptional activation domains consist of peptides comprising D-amino acids,
   wherein the plurality of DNA binding domains comprise one of oligonucleotides, small molecules, and peptide nucleic acids, and
   wherein the ratios of nuclear localization signals and DNA binding domains to activation domains are effective to ensure sufficient nuclear uptake and provide a binding affinity essentially equivalent to naturally-occurring DNA binding proteins.

2. The biologically active synthetic nanoparticle construct of claim 1 wherein the biologically inert substrate is selected from the group consisting of: gold nanoparticles, magnetic nanoparticles, magnetic-core shell nanoparticles, silica nanoparticles, mesoporous nanoparticles, quantum dots, supramolecular nanoparticles, and polymer-based nanoparticles.

3. The biologically active synthetic nanoparticle construct of claim 1 wherein the plurality of DNA binding domains is selected from the group consisting of: hairpin polyamides, zinc finger domains, triple forming oligonucleotides, transcription activator-like effectors, oligonucleotide analogs, locked-nucleic acids, peptide nucleic acids, and combinations thereof.

4. The biologically active synthetic nanoparticle construct of claim 3, wherein the plurality of DNA binding are hairpin polyamides, and wherein the hairpin polyamides comprise at least one N-methyl-imidazole moiety or at least one N-methyl pyrrole moiety, or combinations thereof, arranged sequentially on said polyamide to bind a target gene.

5. The biologically active synthetic nanoparticle construct of claim 1 wherein the plurality of nuclear localization signals are attached to the surface of the biologically inert substrate by crosslinking molecules and wherein the plurality of DNA binding domains are attached to the surface of the biologically inert substrate by crosslinking molecules.

6. The biologically active synthetic nanoparticle construct of claim 1 wherein the plurality of nuclear localization signals are derived from a SV-40 antigen, derived form an HIV-1 antigen, or derived from the group consisting of: TAT, Penetratin, MAP, Transportin/TP10, VP22, MPG, Pep1, pVEC, YTA2, YTA4, M918, CADY, and combinations thereof.

7. The biologically active synthetic nanoparticle construct of claim 1 wherein the plurality of nuclear localization signals follow the Chelsky sequence.

8. The biologically active synthetic nanoparticle construct of claim 1 wherein the plurality of nuclear localization signals are non-classical.

9. The biologically active synthetic nanoparticle construct of claim 1 wherein the biologically inert substrate comprises a gold nanoparticle.

10. A biologically active synthetic nanoparticle construct comprising:
   i. a biologically inert substrate;
   ii. a plurality of single copies of DNA binding domains;
   iii. a plurality of single copies of nuclear localization signals; and
   iv. a plurality of single copies of transcriptional repression domains,
   wherein the plurality of DNA binding domains are each individually covalently attached to a surface of the biologically inert substrate,
   wherein the plurality of nuclear localization signals are each individually covalently attached to the surface of the biologically inert substrate,
   wherein the plurality of transcriptional repression domains are each individually covalently attached to the surface of the biologically inert substrate,
   wherein the plurality of transcriptional repression domains consist of peptides comprising D-amino acids,
   wherein the plurality of DNA binding domains comprise one of oligonucleotides, small molecules, and peptide nucleic acids, and
   wherein the ratios of nuclear localization signals and DNA binding domains to transcriptional repression domains are effective to ensure sufficient nuclear uptake and provide a binding affinity essentially equivalent to naturally-occurring DNA binding proteins.

11. The biologically active synthetic nanoparticle of claim 10 wherein the biologically inert substrate is selected from the group consisting of: gold nanoparticles, magnetic nanoparticles, magnetic-core shell nanoparticles, silica nanoparticles, mesoporous nanoparticles, quantum dots, supramolecular nanoparticles, and polymer-based nanoparticles.

12. The biologically active synthetic nanoparticle construct of claim 10 wherein the plurality of DNA binding domains is selected from the group consisting of: hairpin polyamides, zinc finger domains, triple forming oligonucleotides, transcription activator-like effectors, oligonucleotide analogs, locked-nucleic acids, peptide nucleic acids, and combinations thereof.

13. The biologically active synthetic nanoparticle construct of claim 12 wherein the plurality of DNA binding are hairpin polyamides, and wherein the hairpin polyamides comprise at least one N-methyl-imidazole moiety or at least one N-methyl pyrrole moiety, or combinations thereof, arranged sequentially on said polyamide to bind a target gene.

14. The biologically active synthetic nanoparticle construct of claim 10 wherein the plurality of nuclear localization signals are attached to the surface of the biologically inert substrate by crosslinking molecules and wherein the plurality of DNA binding domains are attached to the surface of the biologically inert substrate by crosslinking molecules.

15. The biologically active synthetic nanoparticle construct of claim 10 wherein the plurality of nuclear localization signals are derived from a SV-40 antigen, derived form an HIV-1 antigen, or derived from the group consisting of: TAT, Penetratin, MAP, Transportin/TP10, VP22, MPG, Pep1, pVEC, YTA2, YTA4, M918, CADY, and combinations thereof.

16. The biologically active synthetic nanoparticle construct of claim 10 wherein the plurality of nuclear localization signals follow the Chelsky sequence.

17. The biologically active synthetic nanoparticle construct of claim 10 wherein the plurality of nuclear localization signals are non-classical.

18. The biologically active synthetic nanoparticle construct of claim 10 wherein the biologically inert substrate comprises a gold nanoparticle.

* * * * *

UNITED STATES PATENT AND TRADEMARK OFFICE
CERTIFICATE OF CORRECTION

PATENT NO. : 10,100,332 B2
APPLICATION NO. : 14/913804
DATED : October 16, 2018
INVENTOR(S) : Lee et al.

It is certified that error appears in the above-identified patent and that said Letters Patent is hereby corrected as shown below:

In the Specification

At Column 1, Line number 20, reads:
"The invention described herein was supported in whole or in part by grants from the National Institutes of Health (New Innovator Award No. NIH-1DP20D006462-01). The U.S. Government has certain rights in this invention."

Should read:
--This invention was made with government support under grant number OD006462 awarded by the National Institutes of Health. The government has certain rights in the invention.--

Signed and Sealed this
First Day of March, 2022

Drew Hirshfeld
*Performing the Functions and Duties of the*
*Under Secretary of Commerce for Intellectual Property and*
*Director of the United States Patent and Trademark Office*